(12) United States Patent  
Bonageri et al.

(10) Patent No.: US 11,526,953 B2  
(45) Date of Patent: Dec. 13, 2022

(54) MACHINE LEARNING TECHNIQUES FOR AUTOMATIC EVALUATION OF CLINICAL TRIAL DATA

(71) Applicant: IQVIA Inc., Parsippany, NJ (US)

(72) Inventors: Virupaxkumar Bonageri, Bangalore (IN); Rajneesh Patil, Durham, NC (US); Nithyanandan Thangavelu, Bangalore (IN); Jian Huang, Parsippany, NJ (US); Vijay Pratap A, Bangalore (IN)

(73) Assignee: IQVIA Inc., Parsippany, NJ (US)

( * ) Notice: Subject to any disclaimer, the term of this patent is extended or adjusted under 35 U.S.C. 154(b) by 482 days.

(21) Appl. No.: 16/451,097

(22) Filed: Jun. 25, 2019

(65) Prior Publication Data

US 2020/0410614 A1  Dec. 31, 2020

(51) Int. Cl.
| | |
|---|---|
| *G06Q 50/18* | (2012.01) |
| *G06N 20/00* | (2019.01) |
| *G16H 10/60* | (2018.01) |
| *G16H 10/20* | (2018.01) |

(52) U.S. Cl.
CPC ............ *G06Q 50/18* (2013.01); *G06N 20/00* (2019.01); *G16H 10/20* (2018.01); *G16H 10/60* (2018.01)

(58) Field of Classification Search
CPC ........ G06N 20/00; G06Q 50/18; G16H 10/20; G16H 10/60
See application file for complete search history.

(56) References Cited

U.S. PATENT DOCUMENTS

| | | | | |
|---|---|---|---|---|
| 8,140,353 | B2 * | 3/2012 | Jung | G16H 20/60 705/2 |
| 2004/0267566 | A1 * | 12/2004 | Badgett | G06F 16/951 707/E17.108 |
| 2009/0313045 | A1 * | 12/2009 | Boyce | G16H 10/20 706/45 |
| 2010/0299335 | A1 * | 11/2010 | Gopalakrishnan | G16H 10/60 707/756 |
| 2012/0323796 | A1 * | 12/2012 | Udani | G16H 10/20 705/80 |
| 2013/0332190 | A1 * | 12/2013 | Hoffman | G16H 10/20 705/3 |
| 2014/0289001 | A1 * | 9/2014 | Shelton | G06F 21/6254 705/7.29 |

(Continued)

*Primary Examiner* — Jay M. Patel
(74) *Attorney, Agent, or Firm* — Fish & Richardson P.C.

(57) ABSTRACT

Aspects of the subject matter described in this specification are embodied in systems and methods that utilize machine-learning techniques to evaluate clinical trial data using one or more learning models trained to identify anomalies representing adverse events associated with a clinical trial investigation. In some implementations, investigation data collected at a clinical trial site is obtained. A set of models corresponding to the clinical trial site is selected. Each model included in the set of models is trained to identify, based on historical investigation data collected at the clinical trial site, a distinct set of one or more indicators that indicate a compliance risk associated with the investigation data. A score for the clinical trial site is determined based on the investigation data relative to the historical investigation data. The score represents a likelihood that the investigation data is associated with at least one indicator representing the compliance risk.

22 Claims, 10 Drawing Sheets

(56) References Cited

U.S. PATENT DOCUMENTS

| | | | |
|---|---|---|---|
| 2014/0324553 A1* | 10/2014 | Rosenberg | G16H 10/20 |
| | | | 705/7.41 |
| 2015/0012482 A1* | 1/2015 | Alsanousi | G16H 10/60 |
| | | | 707/603 |
| 2017/0103190 A1* | 4/2017 | Abraham | G16H 50/30 |
| 2018/0052928 A1* | 2/2018 | Liu | G06F 16/951 |
| 2019/0027232 A1* | 1/2019 | Beim | G16B 50/20 |
| 2019/0304575 A1* | 10/2019 | Beltre | G06N 5/022 |

* cited by examiner

FIG. 4C

MACHINE LEARNING TECHNIQUES FOR AUTOMATIC EVALUATION OF CLINICAL TRIAL DATA

FIELD

The present specification relates to technology for performing data analysis, and more specifically, predictive analytics.

BACKGROUND

Data aggregation can include compiling data from multiple different sources. Depending on the characteristics of the sources from which the data is being compiled, there can be challenges with processing the data to identify data patterns. For example, data obtained from disparate data sources can be in different incompatible formats that require significant processing capabilities to generate indexes used to generate longitudinal mappings. Further, there may be restrictions or other factors that limit access to data from certain providers. Once the data is obtained, from multiple different disparate sources, it can be difficult to effectively present that data in a user interface, particularly, when the data obtained will differ on a per-user basis.

SUMMARY

In general, innovative aspects of the subject matter described in this specification can be embodied in systems and methods that utilize machine-learning techniques to process and evaluate clinical trial data by applying one or more learning models that are trained to identify anomalies representing adverse events associated with a clinical trial investigation. For example, in some instances, the system applies learning models to detect data anomalies present in medical records of patients enrolled in the clinical trial. In other instances, the system applies the learning models to determine the likelihood of a compliance risk associated with a clinical trial due to underreporting, delay reporting, or lack of reporting, of an adverse event associated with treatment of a disease condition.

In one general aspect, subject matter described in this specification may be embodied in a method that includes the operations of: obtaining investigation data collected at a clinical trial site; selecting a set of models corresponding to the clinical trial site, where each model included in the set of models is trained to identify, based on historical investigation data collected at the clinical trial site, a distinct set of one or more indicators that indicate a compliance risk associated with the investigation data; determining, using the set of models, a score for the clinical trial site based on the investigation data relative to the historical investigation data, where the score represents a likelihood that the investigation data is associated with at least one indicator representing the compliance risk; and providing an indication of the compliance risk to the clinical trial site based on the score for the clinical trial site.

These and other versions may each optionally include one or more of the following features. For instance, in some implementations, the compliance risk is associated with a subset of data records identified by the set of models as representing an adverse event specified by a regulatory agency associated with the investigation data.

In some implementations, the compliance risk indicates that all of the data records included in the subset of data records have not been reported to the regulatory agency.

In some implementations, the compliance risk indicates that one or more data records included in the subset of data records have not been reported to the regulatory agency.

In some implementations, the compliance risk indicates that the subset of data records are likely to be reported to the regulatory agency within a time period that exceeds a threshold time period for reporting the adverse event.

In some implementations, the threshold time period for reporting the adverse event is defined by (i) a first time point when the adverse event is discovered, and (ii) a second time point during when the adverse event is reported to the regulatory agency.

In some implementations, the set of models includes a first model that is trained to identify a first set of one or more indicators that represent the compliance risk, and a second model that is trained to identify a second set of one or more indicators that represent the compliance risk. In such implementations, determining the score for the clinical trial site includes the operations of: determining a first sub-score for the investigation data based on processing the investigation data with respect to the first set of one or more indicators; determining a second sub-score for the investigation data based on processing the investigation data with respect to the second set of one or more indicators; and combining the first sub-score and the second sub-score to determine the score for the clinical trial site.

In some implementations, the method also includes the operations of: determining that output provided by the first model is likely to have higher accuracy than output provided by the second model. Additionally, based on determining that the output provided by the first model is likely to have higher accuracy than the output provided by the second model, the method also includes: assigning a first weight to the first score, and assigning a second weight to the second score, where a value of the first weight exceeds a value of the second score. In such implementations, combining the first sub-score and the second sub-score to determine the score for the clinical trial site includes combining the first sub-score and the second sub-score based on the first weight assigned to the first score and the second weight assigned to the second score.

In some implementations, the method also includes the operations of: determining that the score satisfies a threshold value; and based on determining that the score satisfies the threshold value, determining that the clinical trial site is a risk-associated clinical site.

In some implementations, a value of the threshold value is specified by a user that accesses the investigation data.

In some implementations, selecting the set of models corresponding to the clinical trial site includes the operations of: determining one or more attributes associated with the clinical trial site; identifying a set of models that are each trained to process data that represents the one or more attributes; computing, for each model included in the set of models, a relevancy score that reflects a likelihood that a prediction generated by a model is relevant to the investigation data; and selecting, from among the set of models, a subset of models that are determined to have relevancy scores satisfying a threshold.

In another general aspect, subject matter described in this specification may be embodied in a method that includes the operations of: obtaining, from one or more databases, medical records of a clinical trial; identifying one or more lookup parameters associated with the medical records; selecting, based on the one or more lookup parameters, a set of indicators for evaluation of the medical records, where each indicator included in the set of indicators specifies a different condition representing a likely anomaly for a medical record included in the medical records of the clinical trial; determining a subset of medical records from among the medical records, where the subset of medical records are recognized by a model that is trained to identify medical records that satisfy at least one of the conditions specified by the set of indicators; determining, using the model, a score for each medical record included in the subset of medical records; and providing data indicating the scores for output.

These and other versions may each optionally include one or more of the following features. For instance, in some implementations, the scores determined for the subset of medical records represent respective likelihoods that a medical record included in the subset of medical records represents an adverse event associated with the clinical trial.

In some implementations, the one or more lookup parameters includes a lookup parameter indicating a medication associated with the clinical trial.

In some implementations, the set of indicators includes an indicator specifying an expected dosage for the medication.

In some implementations, the subset of medical records includes a medical record associated with a patient that is identified by the model as being prescribed a dosage of the medication that exceeds the expected dosage for the medication.

In some implementations, the one or more lookup parameters include a lookup parameter indicating a disease condition associated with the clinical trial.

In some implementations, the set of indicators includes an indicator specifying an expected treatment plan for the disease condition.

In some implementations, the subset of medical records includes a medical record associated with a treatment event that is identified by the model as being deviating from the expected treatment plan for the disease condition.

Other versions include corresponding systems, apparatus, and computer programs, configured to perform the actions of the methods encoded on computer storage devices.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

FIGS. 4A-D illustrates examples of techniques for predicting compliance risks associated with a clinical trial due to likelihoods associated with an adverse event.

In the drawings, like reference numbers represent corresponding parts throughout.

DETAILED DESCRIPTION

Figure 1:
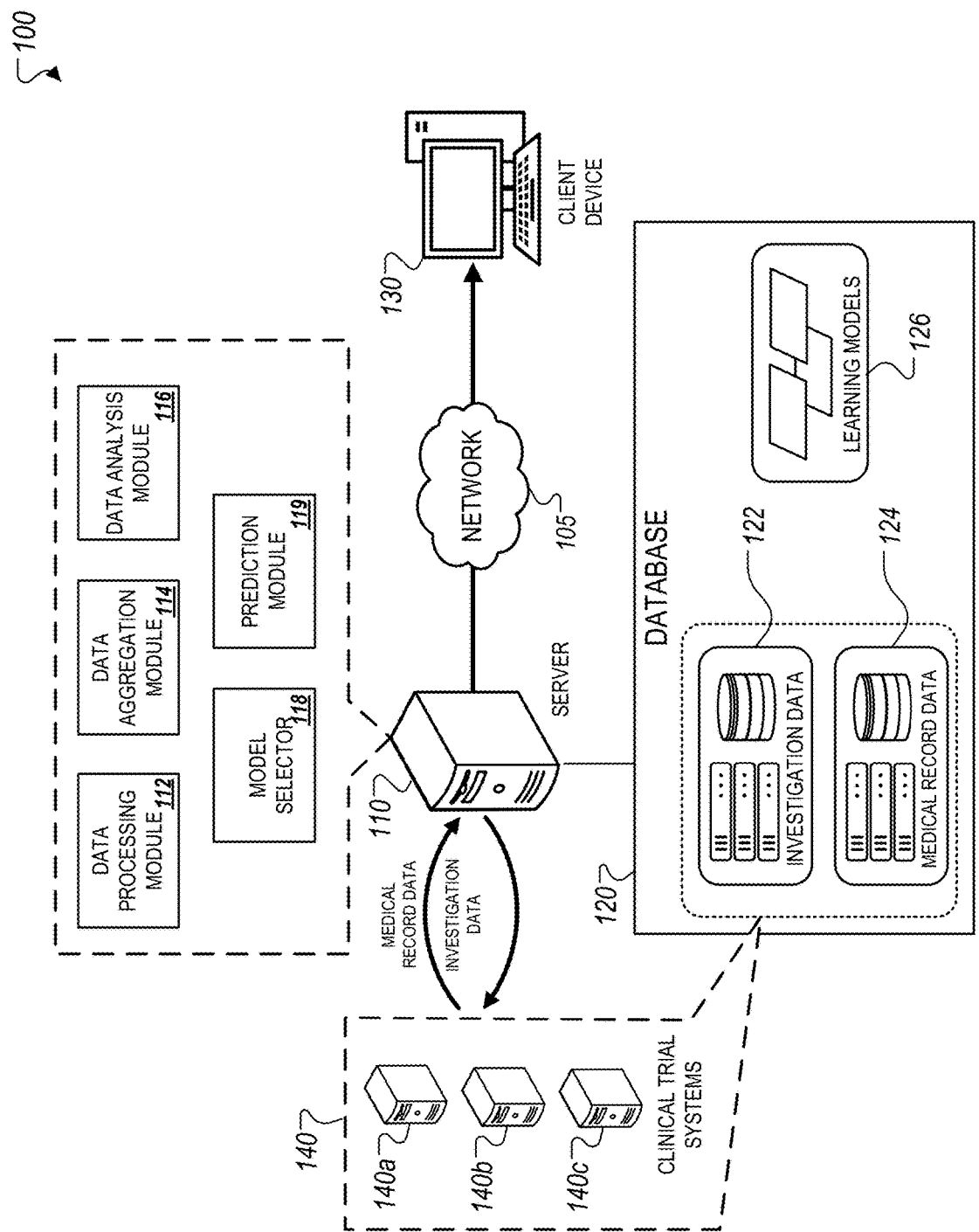
FIG. 1 illustrates an example of a system that computes optimized data predictions for data obtained from multiple disparate data sources.

FIG. 1 illustrates an example of a system 100 that can process and/or evaluate clinical trial data using one or more trained models to identify anomalies representing adverse events. The system 100 includes a server 110, a database 120, and a client device 130 that exchange communications over a network 105. The server 110 further includes a data processing module 112, a data aggregation module 114, a data analysis module 116, a model selector 118, and a prediction module 119. The database 120 stores investigation data 122 associated with a set of database systems, medical record data 124, and learning models 126.

As described throughout, an "adverse event" refers to any event that represents a scientific or medical concern to an ongoing clinical trial investigation. For example, according to Federal Drug Administration (FDA) guidance for clinical trials, an adverse event can represent an event identified during ongoing monitoring of treatment of a disease condition using a pharmaceutical product in drug development and presents a threat to patients seeking medical treatment. Identifying and reporting adverse events during a clinical trial investigation have been a common practice during clinical trials and post-marketing pharmacovigilance.

In some instances, a sponsoring organization or regulatory entity that manages a clinical trial may place requirements on investigators (or investigating organizations) to monitor and/or report any adverse that are identified during an ongoing clinical trial. If such requirements are not met, then the sponsoring organization or regulatory entity may determine that the investigators have unsatisfactorily reported or monitoring adverse events during the clinical trial. As examples, unsatisfactory adverse event reporting typically involves non-reporting (e.g., failing to report an identified adverse event), under-reporting (e.g., providing insufficient or partial information associated with an identified adverse event), or delayed reporting (e.g., failing an identified adverse event in a timely manner, which imposes health risks to patients participating in the clinical trial).

In general, the system 100 obtains, processes, and aggregates streams of encrypted clinical trial data obtained from multiple disparate database systems and uses the data to perform various types of automated predictions (e.g., with minimal or no human intervention). For example, the system 100 can apply the learning models 126 to identify any data anomalies that may be present in the medical records data 124. As another example, the system 100 can apply the learning models 126 to determine likelihoods that patterns identified in the investigation data 122 may create compliance risks for an associated clinical trial. Predictions associated with the investigation data 122 enable clinical trial investigators (or an entity that manages clinical trials) to identify clinical trial sites with high risks of underreporting of adverse events. Evaluation of medical record data 124 to identify data anomalies can be used to produce accurate and consistent results among clinical trial sites and among studies involving multiple clinical trial sites.

Referring now to the components of the system 100, the server 110 can be a device of a service provider (e.g., a data service provider) that enables the access and aggregation of clinical trial data, such as those described throughout this specification. The server 110 can include one or more processors, one or more storage devices (e.g., the database 120) storing instructions that cause the processors to perform certain data processing operations as discussed below.

The server 110 is in communication with the database 120 to perform various operations described throughout. For example, the server 110 can obtain investigation data 122 and/or medical record data 124 from multiple disparate database systems 140 over the network 105. The server 110 can obtain data as a stream of updates in which data packets are periodically transmitted from the database systems 140 to the server 110 over the network 105. In some implementations, the transaction data is obtained based on database queries (e.g., structured query language (SQL) queries) that are executed by the server 110 at certain time periods that cause the extraction of transaction data stored within each of the multiple database systems 140 for storage within the database 120.

The server 110 processes data obtained from the database systems 140 and stores the processed data within the database 120 as investigation data 122 and medical record data 124. The data obtained from the database systems 140 can include encrypted streams of data in multiple incompatible formats. For example, medical record data can be obtained from two database systems that use different encryption techniques to de-identify stored personally identifiable patient information. In other examples, investigation data of different clinical trials can be obtained in different file formats that are processed using different data importing techniques (e.g., importing a ".Zcsv" or a ".txt" file). In some other examples, the obtained data from the multiple database systems 140 can have different database schema and/or logical organizations that impose constraints on how data fields are imported into the database 120.

The server 110 can process data fields (or data packets) included within the streams of data to, for example, decrypt transaction information used to compute various metrics. Other operations can include generating longitudinal mappings that enable data prediction mapping between different database systems. For example, corresponding data fields that are labeled and/or indexed differently within the multiple database systems 140 can be associated with one another in a longitudinal mapping that identifies the corresponding data fields. The server 110 can then use the longitudinal mapping to identify the corresponding data fields in order to make predictions involving transaction information from multiple transaction sources. For instance, the server 110 can use a longitudinal mapping that associates patient visit field and clinical trial identifier to determine a total number of patient visits that are associated with an ongoing clinical trial within, for example, a geographic region.

The server 110 can also generate aggregate data structures that efficiently store obtained information in a more accessible format. For example, the server 110 can extract portions of raw medical record data obtained from the multiple database systems 140 and store extracted portions in a single row and/or column of the database 120. In this example, instead of arranging the obtained transaction data by transaction source, the server 110 instead arranges the obtained transaction data by data field (irrespective of transaction source), which can be used to reduce the number of database queries that are necessary to perform a prediction that involves accumulating information from the multiple transaction sources.

For example, the server 110 can invoke a single database query to access relevant medical record data stored within a row and/or column of an aggregate data structure instead of necessitating multiple database queries to access the same type of data from multiple data structures. This can be accomplished by generating an indexed database record that enables the server 110 to filter, search, and/or parallel process processed data obtained from multiple disparate data sources and stored within the aggregate data structure. Such a configuration may be organized by triggering criteria such that the data structure is only generated for that subset of the range associated with the triggering criteria. In addition, the data structure may be configured to add and index impactful values while excluding values determined to lack impact across the range. Different functions may be applied for different learning models for each context, i.e., those configurations for which one or more triggering conditions are invoked on the system 100. Other types of data processing operations are contemplated within this document, and described in detail below.

The data processing techniques performed by the server 110 can be used to improve various operations performed by the server 110 and other computing devices of the system 100 using the data obtained from the multiple database systems 140. For example, as described above, the server 110 can process obtained data such that multiple encrypted transaction information (e.g., clinical trial investigation data, patient health data, prescriber prescription data, pharmaceutical distribution data, etc.) obtained from different database systems (e.g., health provider systems, medical facility systems, electronic medical record systems, etc.) are processed such that data fields storing transaction information are reorganized and aggregated into database structures that compile information associated with specific data indexes (e.g., investigator identifier, patient identifier, etc.).

The newly generated database structures, as discussed above, enable the server 110, or other devices of the system 100, to more efficiently store pertinent clinical trial data (e.g., data that is used to identify trends and/or patterns that are reflected as metrics). For example, using the data processing techniques described above, the server 110 can store only a subset of the obtained transaction data that are likely to be reflective of, for example, adverse events and/or treatment patterns, and discard other types of information (e.g., source-specific data that is unlikely to relevant to other database systems), thereby reducing the total storage required on the database 120 to adequately store the obtained data as longitudinal data. This can be accomplished using a set of known data field identifiers and/or terms that the server 110 uses to automatically (e.g., without human intervention) identify data fields from multiple transaction sources that store data that is relevant to a particular metric to be computed.

For example, in evaluating treatment patterns for a group of clinical trial investigators associated with a specific clinical trial to identify possible data anomalies, the server 110 can use relevant data field identifiers (e.g., "TREAT," "EVALUATE," etc.) to identify data fields that are likely to include investigation data and non-relevant data field identifies (e.g., "SEX," "AGE," "ETHNICITY") that are less likely to represent anomalies. The identified data fields can be used to filter out data fields that include patient demographic information that is unlikely to be relevant to identifying data anomalies. In other implementations, the server 110 can identify relevant fields based on using the data type of the data stored within each data field (e.g., text data, numerical data, etc.), data type restrictions associated with each data field (e.g., decimal, integer, alphanumeric), among other factors.

As another example, using the techniques described above, the server 110 generates a set of data indicators that can then be used to more quickly access transaction data stored within the investigation data 122 and/or the medical record data 124 when performing data prediction operations such as aggregating investigation data over time periods to compute metrics. By reorganizing and standardizing the data obtained from multiple data sources (which are often stored in incompatible formats as discussed above) within the database 120, computing resources that are necessary to perform such data operations may be reduced. For example, when performing predictions for data stored in the database 120, the number of database queries needed to be executed to obtain pertinent transaction information can be reduced relative to that which may be required to obtain the same information from individual data files obtained from the multiple database systems 140 in a disaggregated format.

In another example, by using aggregate data structures that logically arrange corresponding data fields obtained from multiple transaction sources (as opposed to data arranged according to each transaction source), the server 110 can reduce the sequence of queries that are needed to access transaction data. For example, when performing a data prediction in real-time, the lack of aggregate data structures may necessitate execute a first query to access data obtained from multiple transaction sources, a second query to filter the obtained data to identify relevant data fields, a third query to obtain the identified data from different locations of the database, and a fourth query to move the obtained data into memory to perform a specified data operation. In contrast, with the use of the aggregate data structures described above, the server 110 can run a single query to access data stored within the aggregate data structure, which is predetermined to include corresponding data fields associated with multiple transaction sources, and is arranged such that only relevant data is stored within the aggregate data structure.

The server 110 can be associated with a service provider that enables management of access to transaction data of entities within a healthcare provider network (e.g., prescribers, patients, healthcare facilities, health management organizations, pharmaceutical manufacturers, pharmaceutical distributors, etc.). For example, the server 110 can allow a third-party data provider that is independent from the organizations associated with the database systems 140 to manage, host, and control access to transaction data in accordance with applicable regulatory requirements (e.g., in compliance with the data privacy requirements imposed by Health Insurance Portable and Accountability Act (HIPAA)). In this example, the transaction data is maintained by third-party data providers that provide services to employees based on agreements with the employer. The server 110, therefore, can operate as an intermediary device that is capable of accessing clinical trial data from different independent organizations. The accessed transaction data can be aggregated and presented on a user interface presented through the client device 130.

The database 120 stores various types of clinical trial data such as, for example, investigation data 122 obtained from multiple database systems 140, including database systems 140*a*, 140*b*, and 140*c*. The database 120 also stores medical record data 124 associated with, for example, patients enrolled in clinical trials associated with the database systems 140.

The database 120 also stores learning models 126 that are used to evaluate stored data to perform data predictions, such as the detection of data anomalies in the medical records data 124 or determining the likelihood of a compliance risk being present within the investigation data 122. The operations performed by the components of the server 110 in relation to data stored in the database 120 are described in reference to FIG. 2. The learning models 126 can specify a different statistical technique that may be applied by the server 110 to compute data metrics. For example, the learning models 126 can specify the use of different classifiers to that are used to predict the progression of tracked data parameters at a subsequent time. The learning models 126 can include parametric models that make specific assumptions with respect to one or more of the data parameters that characterize underlying data distributions, non-parametric models that make fewer data assumptions, and semi-parametric models that combine aspects of parametric and non-parametric models. Examples of such models can include Bayesian theory models, gradient boosting machine models, deep learning models, among others that are often used in predictive analytics.

The learning models 126 can be used to compute the metrics described throughout. Each learning model specifies a set of one or more predicted analytics techniques that utilize data patterns and/or trends within electronic data to predict the occurrence of a certain condition (e.g., excessive prescribing activity, risk of an adverse event, etc.). In some instances, each learning model is trained to apply an alternative predictive analytic technique to compute corresponding metrics. In this regard, the system 100 selects a particular learning model from among multiple learning models when computing a metric. As described in detail below, the system 100 can use various types of data attributes to determine which learning model to select when computing a metric. These techniques can be used to improve, for instance, computational resources that are necessary to compute the metrics.

The learning models 126 may be nested or focused. For example, a first model may be used across a first range of values appearing in a database. However, a particular context (e.g., input values) may be used to develop and invoke a more accurate learning model for those conditions where it is determined that a second learning model aligns with predicted values. That is, an alternative model with weak correlation across a broader range may in fact be associated with a stronger correlation across a subset of triggering conditions. The triggering conditions may be dynamically identified as representing a basis for stronger correlation, and thus, use of a different learning model. The system 100 then may be configured to invoke those triggering conditions to process newly received values using the different learning model. Such a configuration may realize computational efficiencies as the newly introduced learning model is only invoked on a selective basis. Such an invocation also may limit the size storage required as results associated with the different learning model need not be stored for all contexts and inputs.

The client device 130 can be any type of network-enabled computing device that provides an interface through which an end-user perceives data provided for output by, for example, the server 110. For example, the client device 130 can be one or more of a smartphone, a laptop computing device, a desktop computing device, a tablet computing device, a smart wearable device, among others. The interface provided for output on the client device 130 can be presented through a native application running on the client device 130 (e.g., a mobile application obtained from a content store) or through a webpage (e.g., through a web-based user portal in association with a customer account stored within the database 120).

Figure 2:
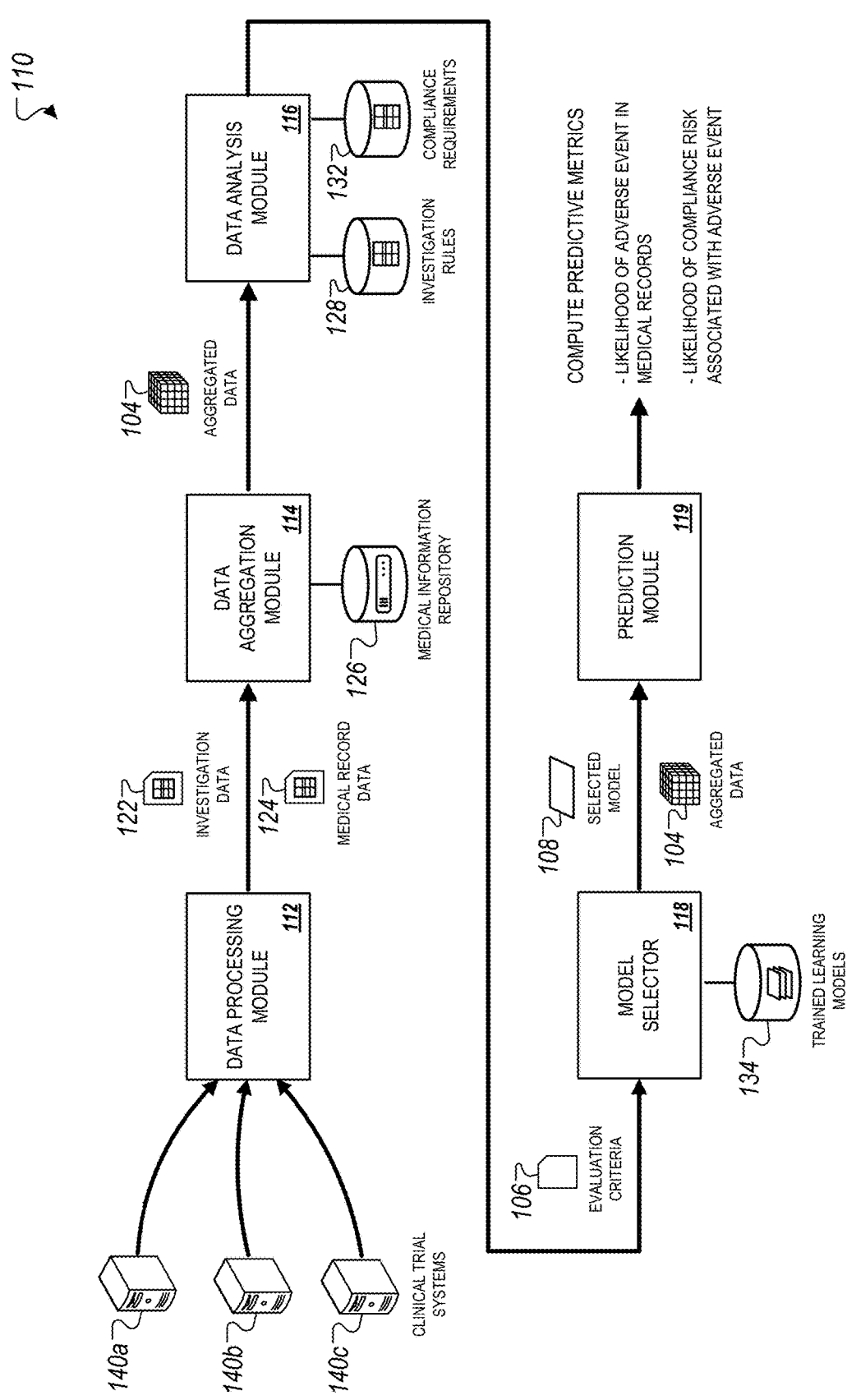
FIG. 2 illustrates examples of data processing techniques that can be applied by the system depicted in FIG. 1.

FIG. 2 is a schematic diagram that depicts example data processing techniques used by the system 100 depicted in FIG. 1. In the example depicted, the operations are performed by components of the server 110, e.g., the data processing module 112, the data aggregation module 114, the data analysis module 116, the model selector 118, and/or the prediction module 119. In other suitable implementations, one or more of the operations depicted in FIG. 2 and described in detail below, can be performed by other components of the system 100 (e.g., the client device 130), or externally by other devices in communication with the system 100 (e.g., an external server in communication with the server 110 over the network 105).

In general, the data processing module 112 obtains streams of encrypted clinical trial data from multiple database systems, for example, the database systems 140a, 140b, and 140c. For example, the obtained data can include investigation data 122. Investigation data 122 can be information that is processed and/or evaluated to determine whether a clinical trial being conducted at a clinical trial site presents one or more compliance risks. Examples of investigation data 122 include, but are not limited to, treatment patterns collected by investigators participating in an ongoing clinical trial, the type of clinical trial being conducted (e.g., a drug efficacy trial), treatment data collected by investigators during patient visits, prescription data associated with treatments, protocols to be followed by investigators when conducting clinical trials at the clinical trial site, or identifications of patient risks or other adverse events. The investigation data 122 also includes medical record data 124 (e.g., medical histories of patients enrolled in an ongoing clinical trial).

In some implementations, the obtained data can include other types of data, such as prescriber data (e.g., a number of prescriptions provided by an individual prescriber over a specified time period, types of prescriptions provided by an individual prescriber), market demographic data (e.g., number of prescribers within a geographic region for which prescriber data is obtained, pharmaceutical distribution data within the geographic region, data that is independent of the individual prescribers for which prescriber data is obtained), and prescriber-specific data (e.g., number of years in practice, healthcare facility affiliations, or other types of prescriber attributes that can impact prescribing behaviors and/or patterns).

In processing the obtained transaction data, the data processing module 112 can filter and/or mine the obtained data for specified transaction information that is determined to be relevant to statistic metrics that are computed based on performing data predictions. For example, the data processing module 112 can obtain raw data (e.g., data stored at the database systems 140 in an unprocessed format) by performing one or more database access queries. The data processing module 112 can filter the raw data for data that is specifically needed to track one or more data parameters (e.g., number of adverse events identified at clinical trial sites, average drug administration dosages for a pharmaceutical product being investigated in a clinical trial, etc.). Data that is not determined to be relevant to tracking the data parameters can be discarded (e.g., not stored within the database 120) such that the storage requirements associated with performing the techniques described throughout are reduced.

The data processing module 112 also indexes data fields within the obtained data to enable the tracking of data parameters, as described above. For example, the data processing module 112 may generate and assign identifiers to data fields, which is then used by the data aggregation module 114 to generate longitudinal mappings that associate data fields of data obtained from different database systems but include related and/or associated information as described above. For example, the data processing module 112 can generate identifiers for each clinical trial investigator (or clinical trial site) such that transaction data of an individual investigator (or individual clinical trial site) obtained from the multiple database systems 140 is indexed to a particular identifier, which can be used to enable the segmentation of obtained clinical trial data by either individual investigator or individual clinical trial site. The data processing module 112 generates investigation data 122 and medical record data 124, which represent indexed data that is transmitted to the data aggregation module 114.

The data aggregation module 114 processes data fields included within the investigation data 122 and/or the medical record data 124 to generate aggregated data 104. For example, the data aggregation module 114 can use the indexes identified within the investigation data 122 and the medical record data 124 to generate longitudinal mappings within the database 120 that associate data fields of clinical trial data obtained from different database systems. In this example, the data aggregation module 114 can generate a new database structure (e.g., a new database table) that only includes data fields that are associated with the longitudinal mapping. In this manner, the aggregated data 104 represents clinical trial data obtained from multiple disparate data sources that has been filtered, sorted, and segmented with respect to various types of hierarchical levels (e.g., individual investigators, individual clinical trial sites, individual drug trials conducted at multiple clinical trial sites, etc.).

In some implementations, the aggregated data 104 can utilize a hierarchal data schema that represents different levels of clinical trial data. For example, the system can obtain clinical trial data of individual investigators, as well as a group of investigators managed by the same sponsoring organization or that conduct clinical trials in the same clinical trial site. In these examples, the data aggregation module 114 stores clinical trial data of individual investigators in the aggregated data 104 within a hierarchal level below the clinical trial data of clinical trial sites such that data redundancies are reduced.

The data analysis module 116 processes contents of the aggregated data 104 to identify data trends and/or patterns of data parameters that are periodically monitored over periods of time. For example, the data analysis module 116 can compute values for data parameters on a periodic basis (e.g., a weekly basis, a monthly basis, etc.). Each time such a computation is performed, the data analysis module 116 filters the contents of the aggregated data 104 to determine the present values of the data parameters. Because streams of transaction data are periodically obtained from the database systems 140, periodic computations of the data parameters can be used to identify progressions that are indicative of data trends. The data analysis module 116 generates evaluation criteria 106, which includes a set of indicators and progression of indicators over time.

As an example, an indicator can be a data attribute that is used to determine a likelihood that the investigation data 122 indicating a compliance risk. For instance, an indicator can be used to determine a likelihood that an adverse event has occurred or will occur in relation to a clinical trial that is being conducted at a clinical trial site. In other instances, an indicator can be used to determine other types of likelihoods associated with reporting of adverse events, such as the likelihood of an adverse event not being reported, the likelihood that an adverse report is under-reported, or a likelihood that an adverse event is reported after unreasonable delay.

As another example, an indicator can represent data attributes that satisfy one or more conditions representing a likely anomaly for a medical record included in the medical records for a clinical trial (e.g., a likely anomaly for a subject referenced in the medical record). For instance, an indicator can identify a disease condition that is not an expected side effect of participating in a clinical trial, which can be used to determine that medical record data represents for a patient exhibiting symptoms for the disease condition represents a likely anomaly. In other instances, an indicator can specify a dosage range for a drug that is permitted for administration during a drug trial. In such instances, the indicator can be used to identify medical record data indicating patients that have received dosages that fall outside the specified dosage range, which can be used to determine that treatment patterns associated with the patients likely represent anomalies for the drug trial.

The model selector 118 selects a learning model 108 from among the learning models 126 to apply in evaluating clinical trial data. The learning model 108 can be selected based on indicators, features, and/or attributes identified within the evaluation criteria 106 that are identified as being relevant to a clinical trial or a clinical trial site. For example, if a clinical trial involves an investigation of efficacy of a drug, the learning model 108 can be trained to identify anomalies within the medical record data 124 that are associated with drug safety, dosage restrictions, or unexpected disease conditions or side effects.

In some implementations, the model selector 118 can additionally, or alternatively, using a scoring scheme to select learning models from among the set of learning models 126. The score can represent a likelihood that a given learning model will generate an output that is relevant to the indicators or features specified in the evaluation criteria 106. In this example, a score threshold can be applied to select only those models that are determined to have a score that satisfies the threshold, or alternatively, select the model with the highest score. In other examples, the scores can be confidence scores representing preliminary assessments as to the accuracy of predictions generated using each model included in the set of learning models 126. For example, learning models that are expected to generate a more accurate prediction can be assigned a higher score value relative to learning models that are expected to generate less accurate predictions.

In some implementations, the model selector 118 can use a dynamic classification rule that specifies the selection of a learning model within the learning models 126 based on, for instance, indicators that are identified as being relevant for a particular clinical trial or clinical trial site. For example, the dynamic classifying rule can specify the selection of a first learning model that is used to identify likely anomalies associated with a clinical trial if the evaluation criteria 106 includes a set of indicators to be used in the evaluation of the medical record data 124. The dynamic classifying rule can specify the selection of a second learning model that is used to determine compliance risks associated with a clinical trial if the evaluation criteria 106 indicates a different set of indicators identifying adverse events and reporting requirements for the adverse events. In some instances, the model selector 118 may select multiple learning models to concurrently perform different types of predictive analytics. For example, the model selector 118 can select both the first and second models to evaluate the medical record data 124 as well as the investigation data 122 in parallel and provide a comprehensive assessment of a clinical trial. In this way, the selection of learning models can be used to tailor and/or customize the predictive analytics that are applied to evaluate clinical trial data and generate predictions based on the evaluation.

In other examples, the dynamic classifying rule can specify the selection of a learning model based on the type of clinical trial data that is identified within the evaluation criteria 106. For example, clinical trial data representing the investigation data 122 can be modeled using a different learning model than clinical trial data relating to the medical record data 124. In these examples, each learning model can be developed using cross-validation techniques applied to the specific type of clinical trial data. For example, a clinical trial model can be cross-validated by being applied to split datasets with known metrics to measure accuracy of predictions generated using the learning model. In addition, real-time metrics can be evaluated against competing scenarios.

As an example, a training dataset that includes clinical trial data collected over a four-year time period can be used to validate metrics predicted using a learning model for a one-year time period. In this example, the system can use data collected in the first three years as development data used to develop and/or train the learning model, and the clinical trial data collected in the fourth year can be used as validation data that is used to cross-validate any predictions made using the learning model, for example, for a fifth year. In addition, the entire data set (e.g., data collected over the four-year time period) can be used as a testing data set that is used to test the model in a deployment environment once the learning model has been developed and validated. During this phase, the system assesses the accuracy of predictions made using the learning model for clinical trial data that has not previously been used to develop, validate, or train the learning model (e.g., a different data set).

In some implementations, one or more new learning models can be added to the set of learning models 126 to promote the progressive development of more detailed or nuanced learning models to be applied by the system 100. That is, if metrics previously computed by existing learning models are determined to be inaccurate, similar learning models that implement more refined predictive analytics techniques can be introduced into the set of learning models 126 to improve overall prediction performance in subsequent evaluation of clinical trial data.

The prediction module 119 generates one or more predictions on aggregate data 104 and computes metrics based on applying the selected learning model 108. For example, the prediction module 119 can apply a regression and/or prediction technique specified by the selected learning model 108 to compute metrics that represent the one or more predictions. Examples of predictions include determining whether the investigation data 122 and/or the medical record data 124 is likely to include an adverse events, determining whether the investigation data 122 presents a certain type of compliance risk related to adverse events, identifying data anomalies within the medical record data 124, among others.

A metric computed by the prediction module 119 can represent different types of data predictions or evaluations. For example, in some instances, the metric represents a numerical value (e.g., a likelihood that a treatment pattern identified for a patient within in the medical record data 124 represents an anomaly relative to treatment patterns identified for other patients). In this example, the prediction module 119 computes a value for the metric based on based on applying a learning model on the number of tracked drug dosages for the same disease condition over a specified time period. In other instances, the metric represents a determination (e.g., whether the investigation data collected at a clinical trial site includes an adverse event). In some other instances, the metric represents a type of classification from among multiple categorizations (e.g., whether the collection of investigation data at a clinical trial site is likely to result in non-reporting, under-reporting, or delayed reporting of an adverse event).

The metrics described above can enable investigators (or entities associated with clinical trials) to perceive predictions or future outcomes presented through a user interface on the client device 130. For example, the metrics can be included in a data report that is provided for output to the client device 130. The data report can identify, for example, clinical trial sites that are predicted to have the highest chance of having an adverse event, types of compliance risks likely to occur due to the adverse events, or monitored patients whose treatment is likely to cause the adverse event. In other examples, the data report can identify other types of data associated with the metrics (e.g., most frequently prescribed pharmaceutical product, most frequently active investigators, etc.). In some implementations, the metrics are computed and provided for output on a periodic basis (e.g., within a monthly data report that is provided for output to the client device 130). Alternatively, in other implementations, the metrics are computed and provided for output on an ad-hoc basis (e.g., in response to a manual request submitted by a user through the client device 130).

Figure 3A:
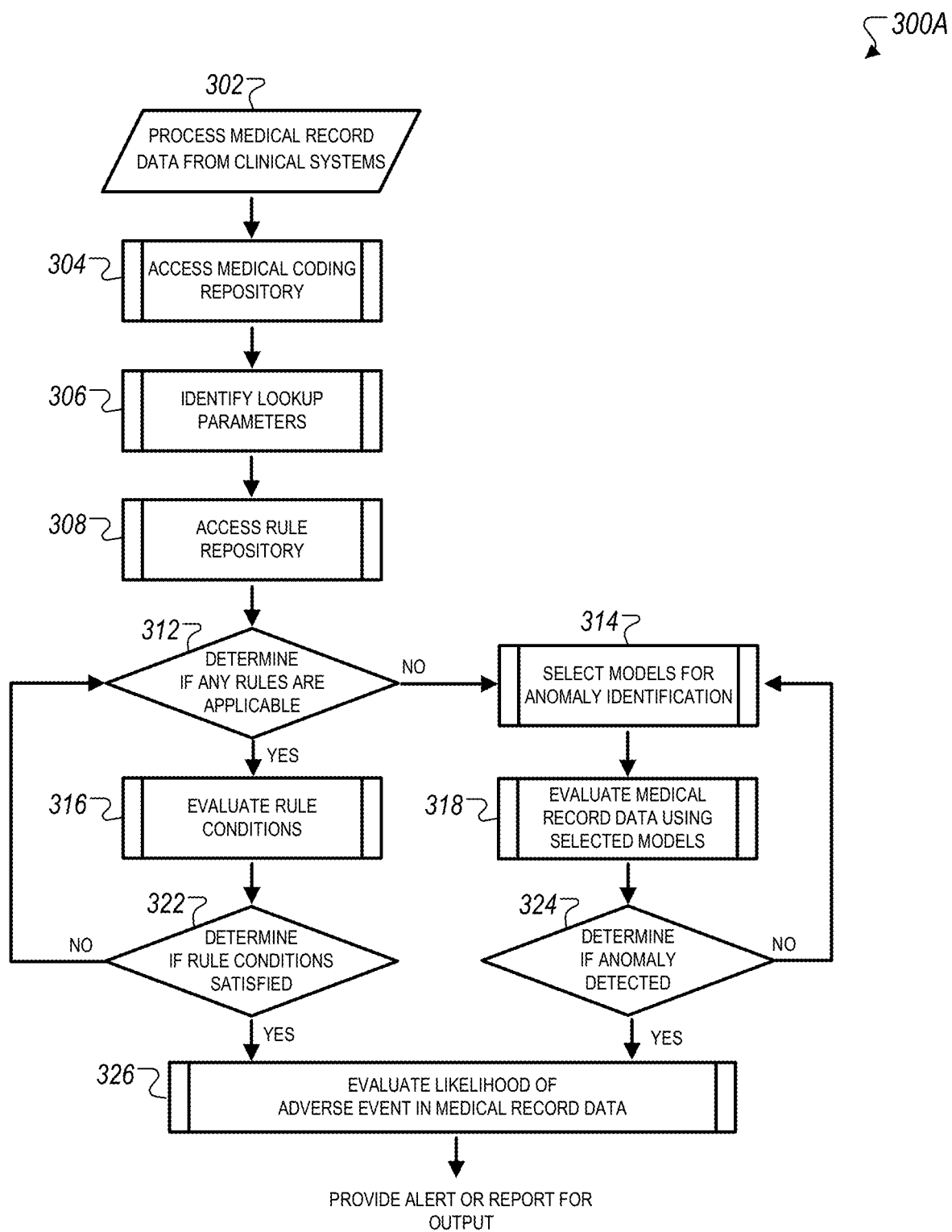
FIGS. 3A-C illustrates examples of techniques for detecting anomalies in electronic medical records associated with clinical trials.
Figure 3B:
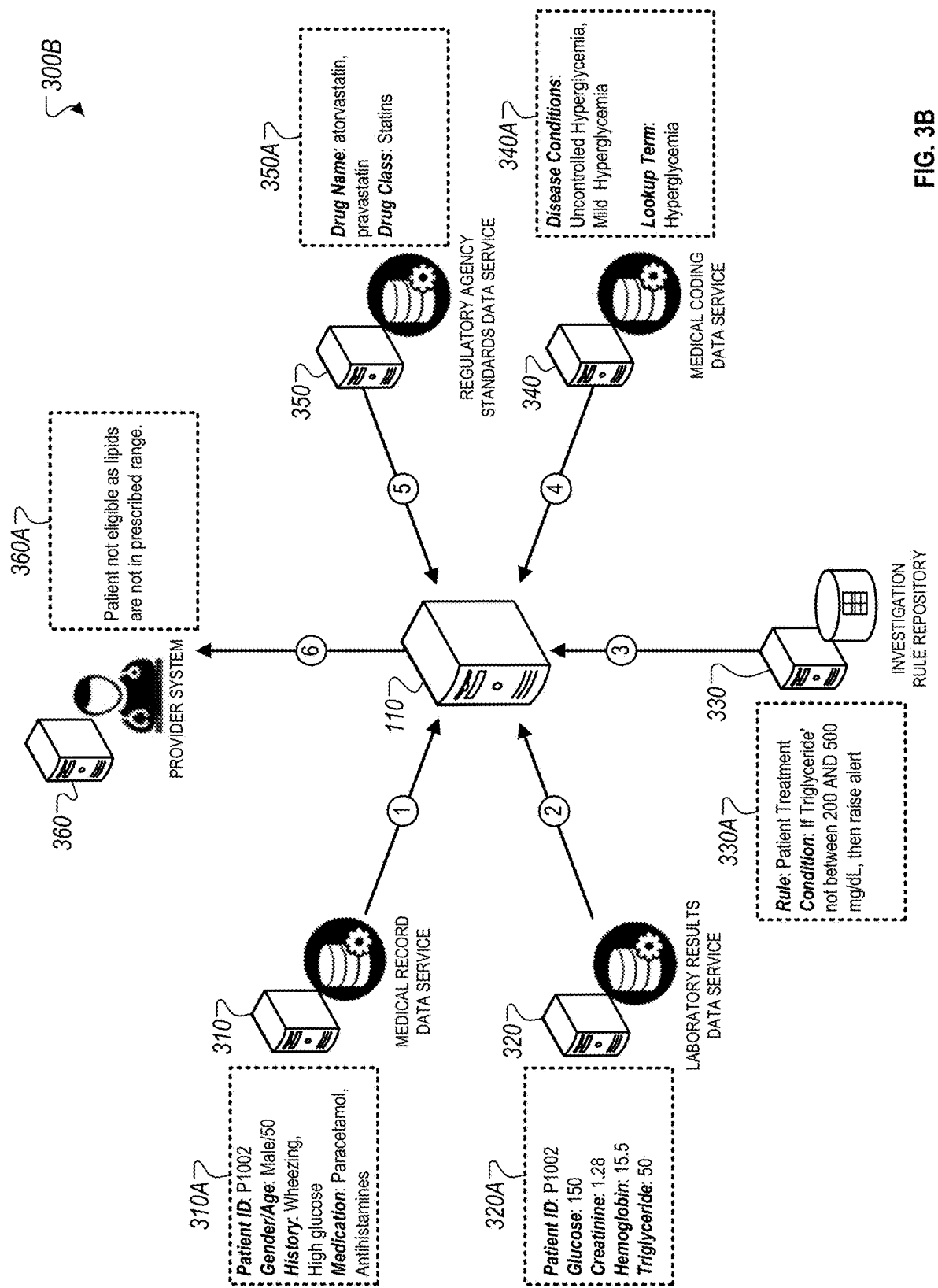
Figure 3C:
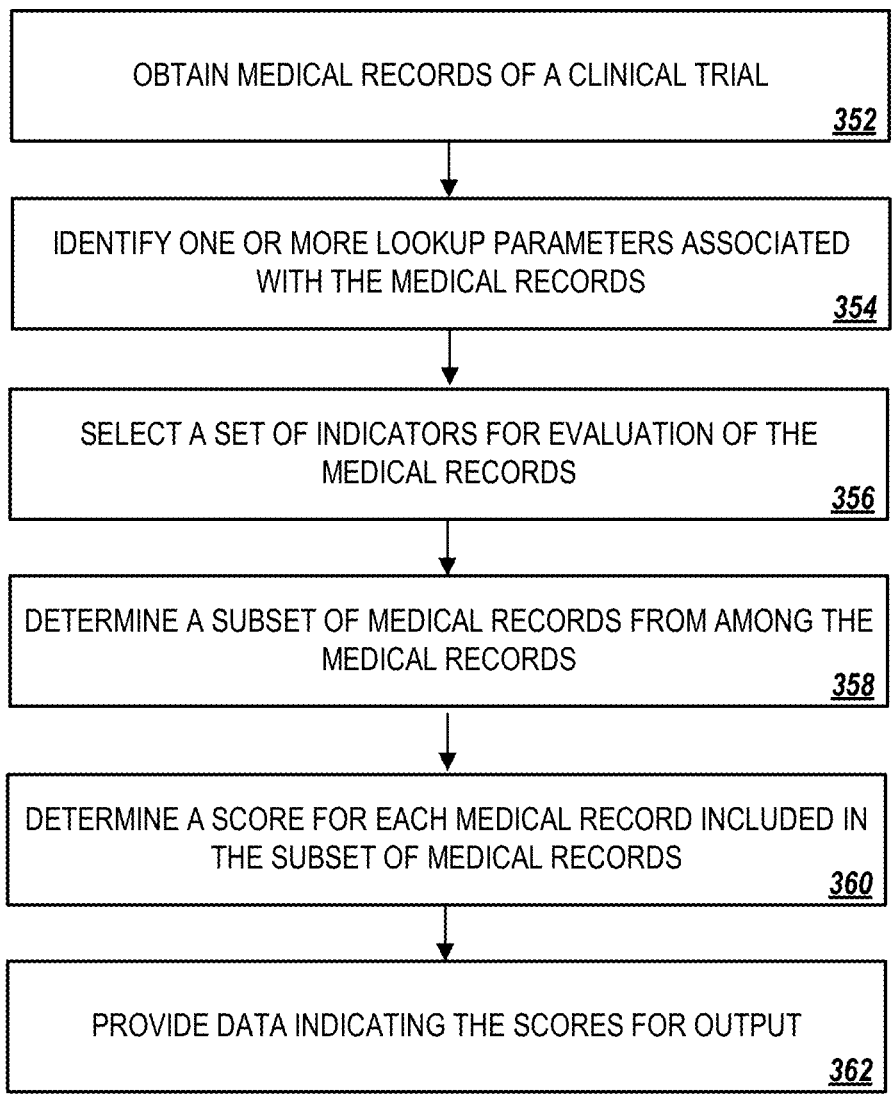

FIGS. 3A-C illustrates examples of techniques for detecting anomalies in electronic medical records associated with clinical trials. Referring initially to FIG. 3A, a process 300A for evaluating electronic medical records using learning models is depicted. At step 302, the medical record data obtained from multiple clinical trial systems is processed. For example, the server 110 obtains medical record data 124 from the set of database systems 140. The medical record data 124 can indicate electronic medical information of patients enrolled in an ongoing clinical trial (e.g., medical history information, health information collected during a recent patient visit, prescribed medications, treatment patterns).

At step 304, a medical coding repository is accessed. For example, the server 110 accesses a medical coding repository that identifies indicators for specific medical codes that may be referenced in the medical record data 124. For instance, the medical coding repository can identify, disease conditions that are associated with a disease code, medications that are frequently prescribed in association with the disease code, or treatment plans that often applied with the disease code.

At step 306, a rule repository is accessed. For example, the server 110 accesses a rule repository that includes rules that can be used to evaluate the medical record data 124. Each rule can specify a condition associated with the indicators that are referenced in the medical coding repository in reference to a given code. For example, a rule can specify conditions for detected dosages that fall outside a permitted dosage range for a medication. In some implementations, the rule repository includes rules specifying conditions corresponding to an adherence protocol of a treatment plan.

At step 312, a determination is made as to whether any rules within the rule repository are applicable to the identified lookup parameters. For example, if the server 110 determines that one or more rules within the rule repository are applicable to the lookup parameters, then the server 110 proceeds to step 318 to evaluate the medical record data 124 using the applicable rules. Alternatively, if the server 110 determines that no rules are applicable to the lookup parameters, then the server 110 proceeds to step 314 to identify learning models for anomaly detection.

At step 314, in some instances if no rules are determined to be applicable to the identified lookup parameters, one or more learning models are selected for anomaly identification. In this circumstance, the server 110 determines that there are no statically defined rules that are likely to be useful in evaluating the medical record data 124 for anomaly detection. The server 110 therefore selects and applies learning models that are trained to identify certain data trends and/or patterns representing likely anomalies for a clinical trial. For example, as described throughout, a learning model can be trained to identify an indicator that represents the existence of an anomaly within the medical record data 124 (e.g., an indication that a treatment pattern for a patient that participates in a clinical trial is not compliant with the treatment protocol for the clinical trial).

At step 318, the medical record data obtained from the clinical trial systems are evaluated using the selected learning models. For example, the server 110 evaluates the medical record data 124 based on learning models that are selected for application from among the set of learning models 126. As described above, learning models can be selected based on attributes specified within the medical record data 124 (e.g., medication used for treatment, disease condition being evaluated in a clinical trial, treatment patterns prescribed by an investigator, etc.). In some instances, the learning models are selected based on their relevancy to lookup parameters, such as names of medications administered to a patient, a disease condition being identified for the patient, or evaluation criteria for the clinical trial as specified by a regulatory agency.

At step 324, a determination is made as to whether the medical record data includes a detected anomaly. For example, the server 110 can compute scores representing respective likelihoods that the medical record data 124 includes a likely anomaly. The scores can be computed by applying selected learning models to identify the occurrence of certain data patterns within the medical record data 124. A score can be computed to have a high value to represent a high likelihood that the medical record data 124 includes an anomaly represented by an indicator evaluated by the one or more selected learning models.

Alternatively, in other scenarios if one or more rules are determined to be applicable to the identified lookup parameters, conditions specified by the applicable rules are evaluated. As described throughout, each of the rules can specify one or more conditions that are used to determine whether the medical record data 124 includes medical records representing a likely anomaly. The conditions specified by the rules can correspond to indicators that are used to identify data anomalies. For example, an indicator can represent a permitted dosage range for a medication to be prescribed to a patient, and a rule can specify conditions indicating that a detected dosage falls outside the permitted dosage range. In other examples, an indicator can be associated with a disease condition for which experimental treatment is being investigated during an ongoing clinical trial. In some other examples, indicators can be associated with disease conditions that patients participating in the clinical trial may have contracted due to a medication being evaluated in the clinical trial.

At step 322, a determination is made as to whether conditions specified by the applicable rules are satisfied. For example, if the server 110 can determine that medical record data 124 satisfies an applicable rule based on determining that one or more conditions specified by the rule have been satisfied. This determination can be used to determine that a likely anomaly exists within the medical record data 124. For example, if a medical record for a patient indicates symptomology that is not characteristic of other patients that are participating in a clinical trial, then the server 110 can apply one or more rules associated with symptomology and determine, based on the application, that the medical record likely represents an anomaly for the clinical trial. In this example, the applied rules can specify conditions representing expected symptomologies.

At step 326, the likelihood of an adverse event being present in the medical record data is evaluated. The server 110 can evaluate the medical record data 124 for the presence of an adverse event regardless of the technique employed to identify the occurrence of anomalies within the medical record data. For example, if the server 110 identifies a likely anomaly within the medical record data 124 at step 322 (i.e., based on applying a static rule) or at step 324 (i.e., based on applying a learning rule), the server 110 can determine whether the anomaly represents an adverse event. As discussed throughout, an adverse event can represent any event that represents a scientific or medical concern to an ongoing clinical trial investigation. Thus, the server 110 can determine that an adverse event has occurred if an identified anomaly represents a scientific or medical concern relating to the clinical trial. For example, if an identified anomaly relates to an unexpected disease condition experienced by a patient enrolled in the clinical trial, and the disease condition creates a health risk beyond the tolerance specified by the clinical trial, then the server 110 can determine that the anomaly represents an adverse event. In contrast, if an identified anomaly deviation from a treatment protocol of a clinical trial but does not produce significant health risks to the patient, then the server 110 can determine that the anomaly does not represent an adverse event. The server 110 then generates a report to include the results of the step 326 and provides the report for output.

Referring now to FIG. 3B, a data processing architecture 300B for evaluating electronic medical records using learning techniques is depicted. The architecture 300B enables the server 110 to exchange communications with various data services in order to evaluate medical record data, as described throughout. The architecture 300B includes a medical record data service 310, a laboratory results data service 320, an investigation rule repository 330, a regulatory agency standards data service 340, a medical coding data service 350, and a provider system 360.

The server 110 utilizes the architecture 300B to perform a set of steps to obtain, process, and evaluate medical record data as described throughout. At step (1), the server 110 obtains medical record data 310A stored at the medical record data service 310. The medical record data 310A is collected the medical record data service 310 after each patient visit, and accumulates information submitted by providers through electronic case forms during the patient visits. For example, the medical record data 310A includes de-identified information associated with a patient medical record, such as a patient identifier, gender, age, and sex. The medical record data 310A can also include a medical history (e.g., high glucose levels) and active medications associated with a treatment plan (e.g., paracetamol, antihistamines).

At step (2), the server 110 obtains laboratory test data 320a from the laboratory results data service 320 for a patient identifier included in the medical record data 310A. For example, the laboratory test data 320A includes a patient identifier, which is used to correlate medical record data and laboratory results data associated with the same patient. The laboratory test data 320A also includes biomarker levels measured for a patient sample (e.g., glucose level, creatinine level, hemoglobin levels, triglyceride levels, etc.).

At step (3), the server 110 accesses an investigation rule repository 330 and identifies rules to be used for evaluating medical record data collected during each patient visit. The rules within the repository 330 can be configured by medical experts, such as healthcare providers, to specify conditions that, when satisfied, indicate that an alert should be generated. For example, a rule corresponding to patient treatment specifies condition that specifies a triglyceride range between 200-500 mg/dl. In this example, the rule condition can be satisfied if a measured triglyceride level is above or below this range, which results in an alert being generated by the system.

At step (4), the server 110 accesses a medical coding data service 340 and uses lookup parameters to identify indicators 340A to evaluate the medical record data 310A. A lookup parameter can be used as an index to, for instance, identify relevant indicators and filter out those indicators that are unlikely to be relevant to the medical record data 310A. For example, the term "hyperglycemia" can be used as a lookup parameter to identify disease conditions associated with the term (e.g., uncontrolled hyperglycemia, mild hyperglycemia). Another example of a lookup parameter is a term representing a name of a medication, which is used to identify disease conditions that are treated using the medication and symptoms commonly experienced by patients after taking the medication. In some other examples, the lookup parameters can include terms that are used to perform lookups in database repositories, such as a drug dictionary, regulatory agency standards, etc.

At step (5), the server 110 accesses a regulatory agency standards data service 350 to identify indicators 350A to be used as reference when evaluating medical record data for anomalies. The indicators 350A can be identified based on lookup parameters applied. For example, the name of a medication can be used as a lookup parameter to identify indicators 350A representing regulatory standards associated with the medication (e.g., dosage ranges, established treatment patterns, risk tolerances for treatments involving the medication, etc.). In some instances, classifications associated with a lookup parameter can be used to identify other related indicators that may be of interest during evaluation. For example, a lookup parameter representing a specific medication (e.g., atorvastatin, pravastatin) can be used to identify additional indicators that are applicable to all drugs that fit a classification of drugs (e.g., statins).

At step (6), the server 110 generates a report 360A indicating results of the medical record data evaluation to a provider system 360. To perform evaluation, the server 110 initially identifies a set of rules specifying conditions associated with the indicators 350A. For example, if an indicator identifies a permitted dosage range for a medication during a clinical trial, a corresponding rule specifies one condition detected dosages that fall below the permitted dosage range, and another condition for detected dosages that are above the permitted dosage. The server 110 applies rules to the medical record data 310A to determine if one or more conditions of the rules are met. For example, if a detected dosage in the medical record data 310A is below the permitted dosage range, then the server 110 determines that a condition specified by the rule is satisfied. In response to this determination, the server 110 generates a report to include an alert indicating that the dosage within the medical record data 310A may not be compliant with regulatory requirements.

In some implementations, the report 360A can include various types of information that may be relevant to a provider. For example, laboratory test data 320A are not in a prescribed range, the report 360A can include an alert notification. As another example, if the server 110 determines that an adverse event has not been reported to the regulatory agency standards data service 350, then the report 360A can include a high priority alert to be reviewed by a medical expert. In some other examples, the report 360A can identify medical records that likely represent anomalies based on evaluation by the server 110 in relation to the indicators 350A.

Referring now to FIG. 3C, an example of a process 300C for detecting anomalies in electronic medical records associated with clinical trials is depicted. Briefly, the process 300C can include the operations of obtaining medical records for a clinical trial (352), identifying one or more lookup parameters associated with the medical records (354), selecting a set of indicators for evaluation of the medical records (356), determining a subset of medical records from among the medical records (358), determining a score for each medical record included in the subset of medical records (360), and providing data indicating the scores for output (362).

In more detail, the process 300C can include the operation of obtaining medical records for a clinical trial (352). For example, the server 110 can obtain medical record data 124 from the set of database systems 140. As described throughout, the medical record data 124 can include electronic information specified in medical records associated with an ongoing clinical trial. For example, the medical record data 124 can include medical histories of patients participating in a clinical trial, patient visit data for the clinical trial, investigation criteria for the clinical trials, among other types of information.

The process 300C can include the operation of identifying one or more lookup parameters associated with the medical records (354). For example, the server 110 can identify one or more lookup parameters associated with the medical record data 124. Examples of lookup parameters include a medication that is associated with a clinical trial (e.g., a pharmaceutical drug that is being evaluated in a drug trial), a disease condition for which treatment is being evaluated for in a clinical trial, among others.

The process 300C can include the operation of selecting a set of indicators for evaluation of the medical records (356). For example, the server 110 can select a set of indicators that are to be used for evaluation of medical records included in the medical record data 124. Each indicator included in the set of indicators can specify a different condition representing a likely anomaly for a medical record included in the medical records for the clinical trial. The set of indicators can be used to as evaluation criteria to identify possible anomalies within the medical record data 124. For example, a medication lookup parameter can be used to select an indicator that represents a permitted range of dosages of the medication for administration during the clinical trial, as specified by a regulatory agency that oversees the clinical trial. In this example, the server 110 evaluates dosages recorded in the medical record data 124 in relation to the set of range of permitted dosages, and determines that medical records that identify administered dosages falling outside the range as possible anomalies.

The process 300C can include the operation of determining a subset of medical records from among the medical records (358). For example, the server 110 can determine a subset of medical records from among the medical record data 124 that represent likely anomalies based on the selected set of indicators. As described throughout, the subset of medical records can be identified based on the electronic information being recognized by a learning model as being anomalous given the selected set of indicators. The learning model can be trained to identify medical records that satisfy at least one of the conditions specified by the set of indicators, and thereby identify medical records (i.e., the subset of medical records) that are likely to represent a data anomaly. For example, a medical record that indicates an unusual treatment pattern for a patient can be identified as an anomaly and used to determine whether an investigator has properly following clinical trial protocol for administering a regulated medication.

The process 300C can include the operation of determining a score for each medical record included in the subset of medical records (360). For example, the server 110 can determine a score for each medical record included in the subset of medical records based using the learning model. As described throughout, each score can represent a respective likelihood that a certain medical record included in the subset of medical records is associated with an adverse event. For example, a score with a value of 0.32 can represent a 32 percent probability that medical record information for a patient collected during a recent visit indicates that the patient may have experienced a stroke. In this example, the computed score is used to indicate that the patient may have experienced an unexpected side effect of the clinical trial, and that the risk posed by the clinical trial to the unexpected side effect exceeds a predetermined threshold (e.g., 10 percent), which likely indicates that an adverse event has occurred.

The process 300C can include the operation of providing data indicating the scores for output (362). For example, the server 110 can generate a report that includes the score and provides the report for output to the client device 130. As discussed throughout, in some implementations, the report is generated periodically at specified time intervals (e.g., daily, weekly, monthly, etc.). In other implementations, the report is generated at specified time points representing a certain milestone of a clinical trial being conducted at the clinical trial site. For example, the report can be generated after a phase of a clinical trial has been concluded, upon completion of clinical experimental data collection, among others. In some other implementations, the report is generated on an ad-hoc basis based on a request made by a user, such as a participating investigator in the clinical trial, or an individual associated with a sponsoring organization that manages the clinical trial.

Figure 4A:
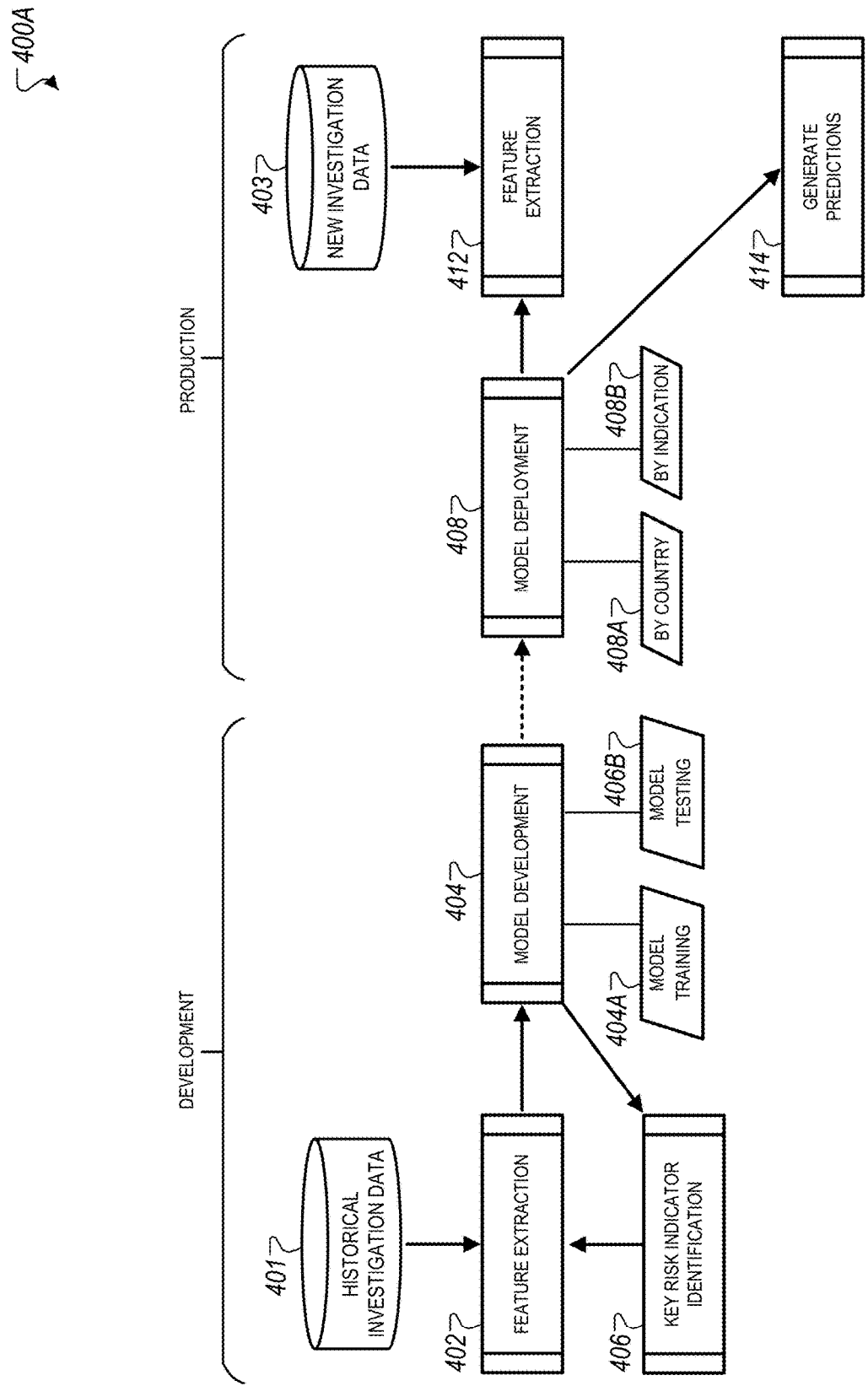

FIGS. 4A-D illustrates examples of techniques for predicting compliance risks associated with a clinical trial due to likelihoods associated with an adverse event. Referring initially to FIG. 4A, an example of a process 400A for training and developing modeling techniques for generating predictions associated with adverse events within clinical trial data is depicted. As shown, the process 400A generally includes two phases—(1) a development phase, and (2) a production phase. During the development phase, a learning model is trained based on historical data, and validated until a desired accuracy and/or precision level for predictions developed using the learning model are achieved for training data. Once the development phase is complete, a trained learning model is deployed in a production environment to clinical trial data (e.g., data obtained from the set of database systems 140) to be evaluated using the system 100.

At 402, predictor features to be applied by the learning models are extracted based on historical investigation data 401. The predictor features can be used to identify a binary outcome of unsatisfactory reporting of adverse events at a clinical trial site up to a given clinical cutoff date. As described throughout, unsatisfactory reporting can be represented as non-reporting of an adverse event, under-reporting of an adverse event, or delay in reporting an adverse event relative to the clinical cutoff date. The binary outcome identifies whether reporting was or was not satisfactory (i.e., "YES" or "NO").

The predictor features can be used to identify clinical trial sites that are predicted to most likely provide unsatisfactory adverse event reporting (e.g., failing to report, under-reporting, or delayed reporting of adverse events). The predictor features can reflect site information and certain performance metrics that are determined based on from historical data associated with each clinical trial site. For examples, the predictor features can be generated based on historical metrics, such as a number of adverse events previously identified at a clinical trial site, a percentage of adverse events that were unsatisfactorily reporting, the frequency of adverse events previously identified within a specified time period, among others. In some instances, the predictor features can be generated to indicate clinical trial sites that are more likely to exhibit unsatisfactory adverse event reporting due to the type of clinical trials being performed at a clinical trial site (e.g., clinical trials involving the collection of data that is more likely to be unsatisfactorily report adverse events).

At 404, learning models are developed using the predictor features. At 404A, learning models are trained using historical investigation data 401. The learning models can employ different types of machine-learning techniques (e.g., logistic model, Random Forest, Gradient Boosting Trees and Neural Networks). In some instances, the historical investigation data 401 includes 80% randomly sampled data. During training, parameters of each type of learning model are tuned to, for example, optimize the Area under the Receiver-Operating-Characteristic Curve (AUC) in a 20% testing data. At 404B, learning models are then tested to identify an optimal model for each machine-learning technique (e.g., a model determined to have the highest AUC in testing). In some instances, external algorithms can also be modified so that they can be combined or stacked to make more accurate and reliable predictions. Once trained, parameters of the optimal learning models are applied to develop predictions in the production phase, as discussed below.

At 406, a list key risk indicators (KRIs) that are used for adverse event detection are identified. KRIs represent factors that may impact the administration of a clinical trial, such as a disease condition being evaluated, medications administered during the clinical trial, a number of patient visits, a number of investigators, a number of related clinical trial sites associated with the same clinical trial investigation, a patient visit volume over a specified time period, among others. The KRIs can be applied to monitor a performance of a clinical trial site as it relates to reporting adverse events. In some instances, the system applies techniques to improve computational efficiencies associated with monitoring. For example, instead of monitoring multiple KRI metrics at each clinical trial site, the system can focus on checking KRIs to gain efficiency with minimal loss in accuracy. KRIs of a target metric can be identified to measure the importance or contribution of predictor features. In each optimized predictive model, the top most important predictor features (e.g., top ten most important) can be determined as the KRIs. The number of predictor features can be adjusted according to, for instance, the total number of predictor features available in the data, and the distribution of feature importance.

At 408, trained models are deployed to evaluate investigation data 403. Trained models can be deployed to perform in at least three configurations: (1) prediction based on the model using all historical data, (2) prediction based on a model developed with respect to certain therapeutic area, and (3) prediction based on a model developed within a given geography (e.g., country). If the investigation data 403 is obtained from a mixed dataset (e.g., mixed therapeutic areas, different countries), then predictions can be made using configuration (1). Alternatively, the investigation data 403 is obtained from a single therapeutic area or a single geography, and training based on the historical investigation data 401 is sufficient with respect to that therapeutic area or that geography are sufficient (e.g., the number of clinical trial sites exceeds one hundred), it may be adequate to make predictions either configures (2) or (3).

At 412, predictor features associated with the investigation data 403 are extracted based on deploying the trained models. The predictor features associated with the investigation data 403 can be extracted in the same manner as previously described above in reference to step 402.

At 414, predictions of adverse events are generated for the new investigation data 403 based on the application of the trained model. For example, probabilities associated with different types of unsatisfactory adverse event reporting can be computed for each clinical trial site based on the deployment of the trained learning models to the investigation data 403 in step 408. In some instances, the probabilities are represented as values that ranging from "0" to "1." In such instances, a threshold value (e.g., 0.65) can be applied to differentiate between clinical trial sites that are identified as being likely to exhibit unsatisfactory adverse event reporting (e.g., probability values exceeding 0.65) and other clinical trial sites that are not likely to exhibit unsatisfactory adverse event reporting (e.g., probability values below 0.65). In some implementations, the threshold value is customizable by a user to balance precision and recall in identifying clinical trial sites that are likely to exhibit unsatisfactory adverse event reporting. In other implementations, a default value of the threshold value (F1) is computed based on a specified equation where F1=2*[(precision)*(recall)]/(precision+recall). In such implementations, a higher threshold value generally tends to improve precision level and decrease the level of recall.

In some implementations, to optimize resource allocation, clinical trial sites can be clustered into multiple (e.g., six) groups according to risk severity, such as the predicted probability of unsatisfactory adverse event reporting. For example, clinical trial sites classified as belong to the sixth group are those that are determined to have predicted probabilities lower than a threshold value. In contrast, clinical trial sites in groups 1 to 5 are those are determined to have issues relating to underreporting of adverse events. In this example, groups 1 to 5 account for 10%, 10%, 20%, 30%, and 30% of signaled sites, respectively.

Figure 4B:
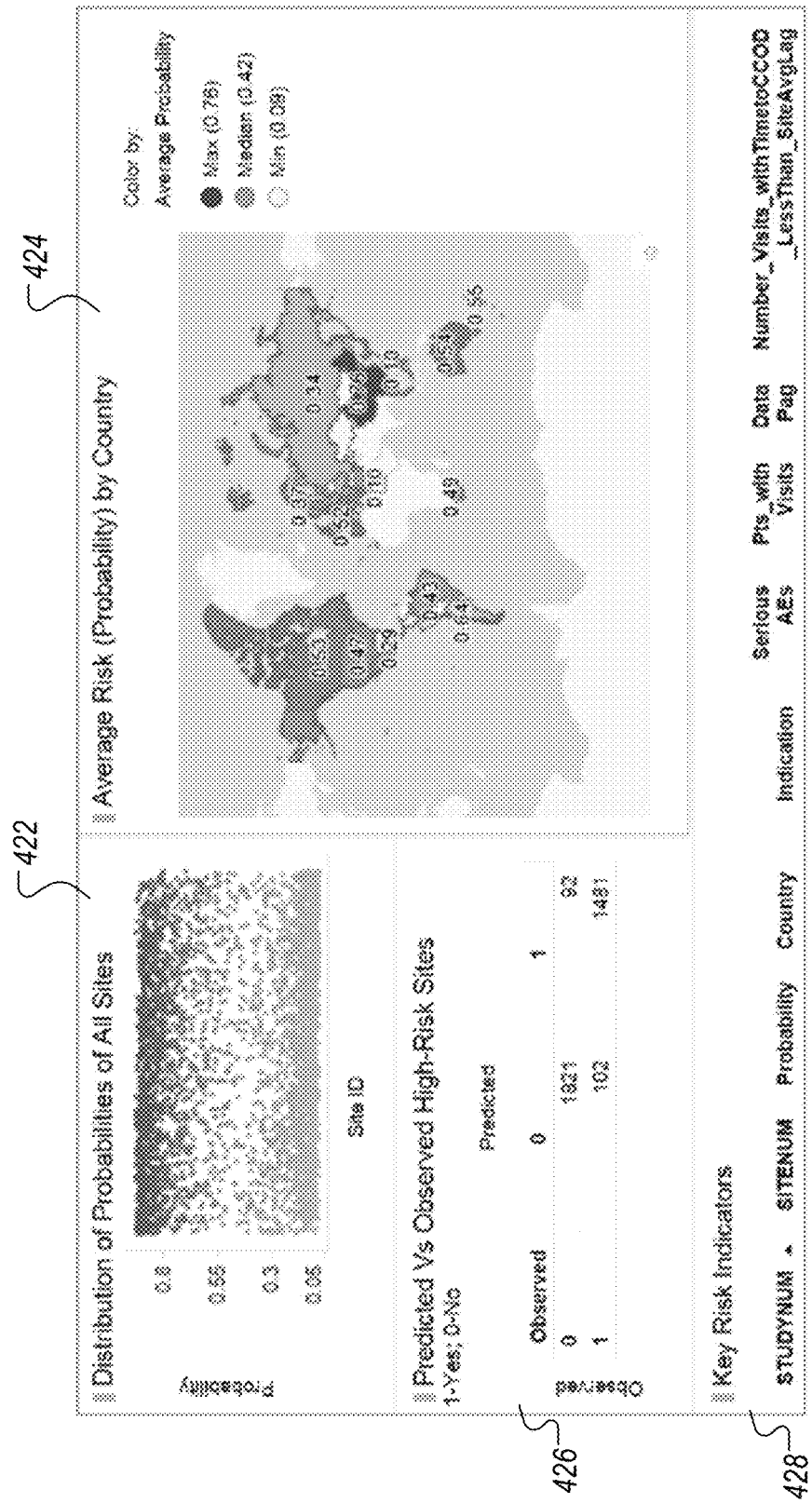
Figure 4C:
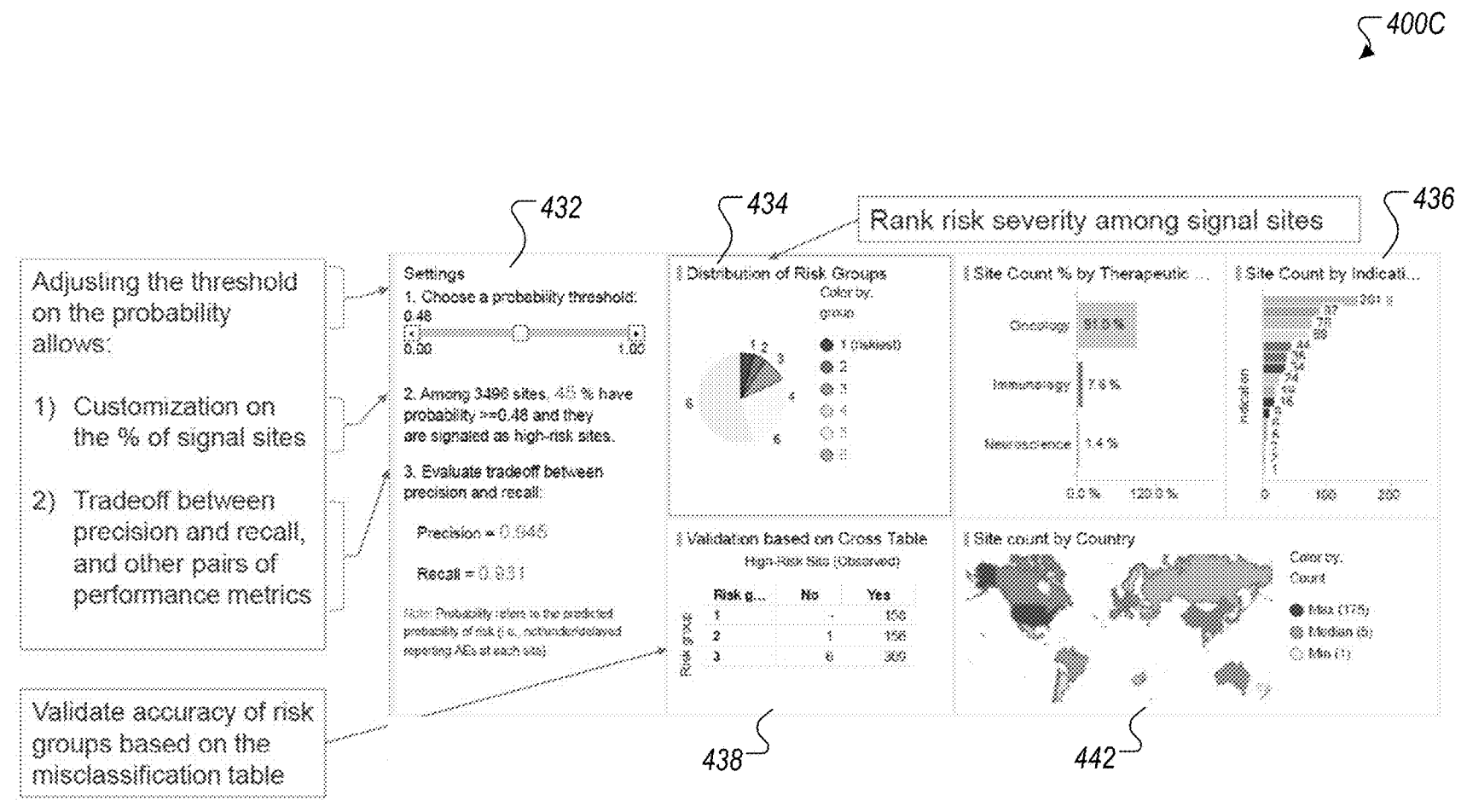

Referring now to FIGS. 4B and 4C, example of interfaces 400B and 400C that can be used to predict clinical trial sites with unsatisfactory reporting of adverse events are depicted. FIG. 4B depicts an interface 400B that can be used to access a distribution of predicted probabilities for insufficient adverse event reporting at multiple clinical trial sites. The interface 400B can be displayed through an application (e.g., web-based application, native application) running on the client device 130 and configured to access data stored in the database 120, such as the investigation data 122 and the medical record data 124.

As shown in FIG. 4B, the interface 400B includes various interface elements that allow a user (e.g., a clinical trial investigator, an individual associated with a regulatory agency or a sponsoring organization of a clinical trial) to access and/or manipulate predictions generated by the system 100. For example, interface element 422 displays a graph representing a distribution of probability scores that computed for multiple clinical trial sites. As described throughout, each probability score represents a likelihood that a clinical trial site will exhibit unsatisfactory adverse event reporting (e.g., underreporting, non-reporting, or delayed reporting of adverse events). Each clinical trial site is assigned a unique site identifier to permit the association of probability scores to corresponding unique site identifiers. The graph displayed in the interface element 422 enables a user to perceive a visual representation of the number of clinical trial sites that are highly likely to exhibit unsatisfactory adverse event reporting (e.g., clinical trial sites with probability scores exceeding a value of 0.65), and those clinical trial sites that are not (e.g., clinical trial sites with probability scores exceeding a value of 0.35).

Interface element 424 displays a graph representing aggregated risk of unsatisfactory adverse event reporting for different geographic regions where clinical trial sites are located. To generate the graph, the system aggregates the probability scores for clinical trial sites located within a certain geographic region (e.g., country) to compute an average probability score for the geographic region. Threshold values can then be used to represent different levels of risks. For example, geographic regions with average probability scores exceeding 0.76 can be designated as "max risk" and a corresponding geographic region in a map can be colored to represent the designation. Although interface element 424 depicts average risk by country, in some instances, other types of geographic regions can be used to represent aggregate average risk (e.g., continents, intra-country territories, etc.).

Interface element 426 displays a table including data that compares observed data and predicted data. Predicted data associated with a clinical trial site indicates a prediction made by the system that the clinical trial site is likely to exhibit unsatisfactory adverse event reporting based on applying one or more learning models, as described throughout. Because predicted data is based on evaluation of investigation data, it represents an assessment of risk that may require validation or confirmation using observed data. Observed data associated with a clinical trial site provides confirmation of whether the clinical trial site actually exhibited unsatisfactory adverse event reporting. In this way, if observed data matches predicted data, then a user can determine that predictions made by the system have a degree of validation.

Interface 428 indicates a list of key risk indicators that are used by one or more learning models to compute a probability score for a clinical trial site. In some implementations, each indicator included in the list of key risk indicators can be assigned a weight representing whether a clinical trial site being associated with the indicator provides a higher or lower risk of unsatisfactory adverse event reporting. For example, if a clinical trial site is located in a country designated as a high-risk country, then the system may positively bias score computation to represent the increased risk of exhibiting unsatisfactory adverse event reporting based on the location of the clinical trial site. As an example, if a clinical trial site involves investigating a certain medication that rarely produces an adverse event during investigation, then this aspect can be used to negatively bias score computation to represent the reduced risk of exhibiting unsatisfactory adverse event reporting. Other examples of key risk indicators include a disease condition associated with a clinical trial, medications administered during the clinical trial, a number of patient visits, a number of investigators, a number of related clinical trial sites associated with the same clinical trial investigation, a patient visit volume over a specified time period, among other factors that may impact the administration of a clinical trial.

Referring now to FIG. 4C depicts an interface 400C that can be used to group individual clinical trial sites into different risk clusters based on prediction data associated with adverse events. The interface 400C can be accessed by a user to customize settings used by the system to identify clinical trial sites that are likely to exhibit unsatisfactory adverse event reporting. For example, interface element 432 includes a slider that enables a user to adjust a threshold value to be used to for designating clinical trial sites as high-risk clinical trial sites. The interface element 432 also displays a percentage of all clinical trial sites that are designated as high-risk clinical trial sites based on a user-specified threshold score, as well as the impacts on precision and recall. A user can use the interface element 432 to evaluate the trade-off between precision and recall as it relates to selecting a threshold score for probability scores.

Interface elements 434, 436, 438, and 442 include visualizations that are adjusted based on the threshold score specified for a probability score in the slider displayed in interface element 432. For instance, interface element 434 displays a graph indicating a distribution of risk groups that are generated based on the user-specified threshold for the probability score. Interface element 436 displays a graph indicating the number of high-risk clinical trial sites that are predicted for each indication (e.g., disease condition, medication) associated with one or more clinical trials. Interface 438 displays a chart that allows a user to validate accuracy of the risk groups identified in the interface element 434 based on observed data for the clinical trial sites. For example, possible misclassifications are identified based on unsatisfactory adverse event reporting that is actually observed at clinical trial sites. Interface element 442 displays a map that displays different colors to represent that number of high-risk clinical trial sites that are included in various geographies.

Figure 4D:
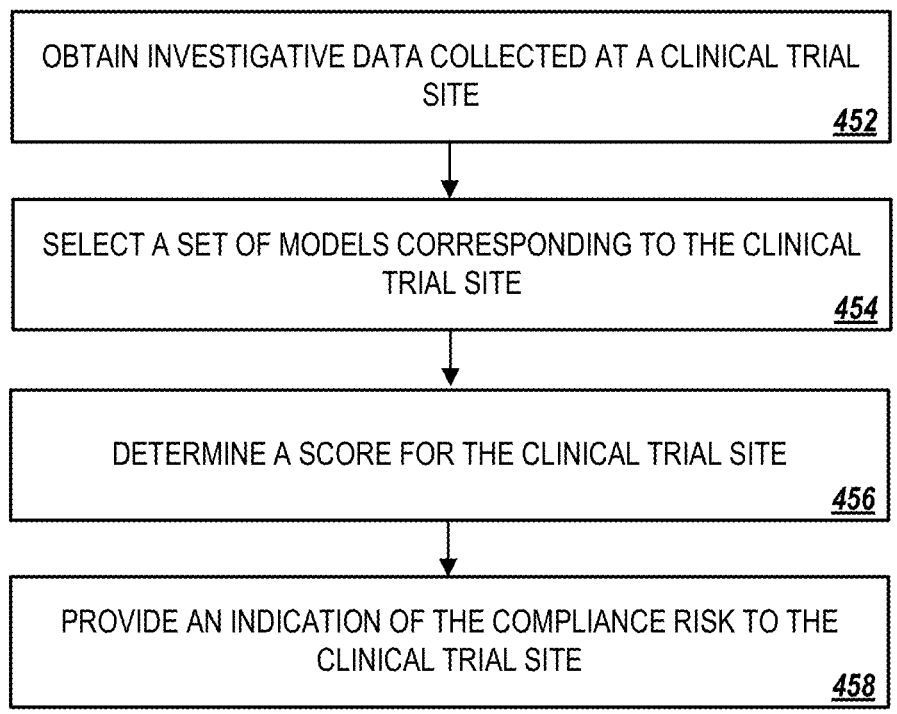

Referring now to FIG. 4D, an example of a process 400D for predicting compliance risks associated with a clinical trial due to likelihoods associated with an adverse event is depicted. Briefly, the process 400D can include the operations of obtaining investigative data collected at a clinical trial site (452), selecting a set of models corresponding to the clinical trial site (454), determining a score for the clinical trial site (456), and providing an indication of the compliance risk to the clinical trial site (458).

In more detail, the process 400D can include the operation of obtaining investigation data collected at a clinical trial site (452). For example, the server 110 can obtain investigation date from a database system included in the set of database systems 140. The database system can be associated with a clinical trial site where the investigation data is collected. As discussed throughout, the investigation data can specify, for example, the type of clinical trial being conducted (e.g., a drug efficacy trial), treatment data collected by investigators during patient visits, prescription data associated with treatments, identifications of patient risks or other adverse events, among others. In some instances, the investigation data can also specify protocols to be followed by investigators when conducting clinical trials at the clinical trial site.

The process 400D can include the operation of selecting a set of models corresponding to the clinical trial site (454). For example, the server 110 can select one or more learning models from the learning model 126 that corresponded to the clinical trial site associated with the investigation data.

Each learning model included in the selected set of models can be trained to identify a distinct set of indicators representing a compliance risk associated with the investigation data in relation to historical investigation data collected at the clinical trial site. For example, one selected learning model can be trained to identify health risks imposed on patients based on medical notes indicating adverse symptoms being reported by patients during prior patient visits. As another example, another selected learning model can be trained to identify the occurrence of a medical condition experienced by a patient as representing an adverse event. In these two examples, the indicators used by the first model can be, for example, morbidity statistics, whereas the indicators used by the second model can be conditions for reporting adverse conditions specified by a sponsoring organization that manages the clinical trial.

The process 400 can include the operation of determining a score for the clinical trial site (456). For example, the server 110 can determine a score the clinical trial site using the selected learning models based on the investigation data relative to the historical investigation data. As described throughout, the score can represent a likelihood that the investigation data is associated with at least one indicator representing a compliance risk. For example, the numerical value of the score can indicate a probability that an adverse event will be identified at the clinical trial site, but not reported to a sponsoring organization or a regulatory agency within specified monitoring requirements. In this example, the score may represent a high probability of an adverse report not being report if, for instance, the historical investigation data indicates a large number of adverse events being identified at the clinical trial site in the last year, a large portion of which were not properly reported according to reporting criteria. In other examples, the compliance risk can represent other types of probabilities, such as the probability of an adverse event being identified during the clinical trial, the probability that the adverse event will be properly reported (e.g., sufficient information associated with the adverse event will be reported), the probability that the adverse event will be reported in a timely manner (e.g., within a designated time period upon identification of the adverse event), among others.

The score can be computed based on combining sub-scores for the set of one or more indicators. For example, a first sub-score can be computed for an indicator that represents a probability that an adverse event will be identified at the clinical trial site, and a second sub-score can be computed for another indicator that represents a probability that any detected adverse event will not reported to a sponsoring organization or a regulatory agency within specified monitoring requirements. The two sub-scores can be combined using specific weights to generate an aggregate score reflecting an overall likelihood that the investigation data represents a compliance risk. In this way, the system uses multiple indicators to balance various different aspects of compliance risks that may be implicated with the investigation data. For example, sub-scores for indicators that reduce the likelihood of a compliance risk can be used to bias the aggregate score relative to sub-scores for other indicators that increase the likelihood of a compliance risk. In other examples, indicators can be used to represent different types of compliance risks, and the aggregate score reflects an overall likelihood that at least one of the different types of compliance risks are associated with the investigation data.

The process 400 can include the operation of providing an indication of the compliance risk to the clinical trial site (458). For example, the server 110 can generate a report that includes the score and provide the report for output to the client device 130 and/or a computing device associated with the clinical trial site. As discussed throughout, in some implementations, the report is generated periodically at specified time intervals (e.g., daily, weekly, monthly, etc.). In other implementations, the report is generated at specified time points representing a certain milestone of a clinical trial being conducted at the clinical trial site. For example, the report can be generated after a phase of a clinical trial has been concluded, upon completion of clinical experimental data collection, among others. In some other implementations, the report is generated on an ad-hoc basis based on a request made by a user, such as a participating investigator in the clinical trial, or an individual associated with a sponsoring organization that manages the clinical trial.

Figure 5:
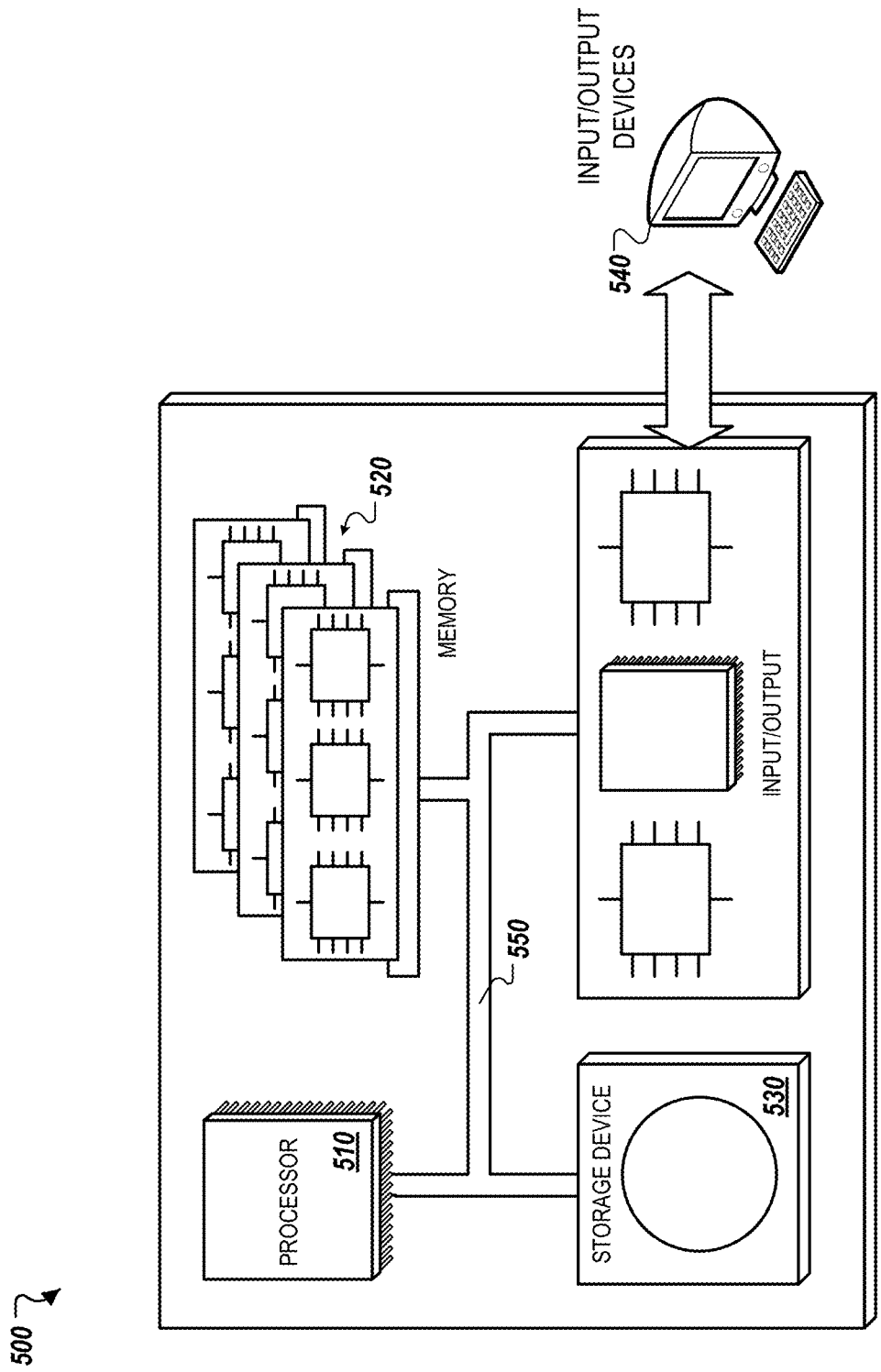
FIG. 5 is a block diagram of computing devices on which the processes described herein, or portions thereof, may be implemented.

FIG. 5 is a schematic diagram of a computer system 500. The system 500 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 500) and their structural equivalents, or in combinations of one or more of them. The system 500 is intended to include various forms of digital computers, such as laptops, desktops, workstations, personal digital assistants, servers, blade servers, mainframes, and other appropriate computers, including vehicles installed on base units or pod units of modular vehicles. The system 500 can also include mobile devices, such as personal digital assistants, cellular telephones, smartphones, and other similar computing devices. Additionally, the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 500 includes a processor 510, a memory 520, a storage device 530, and an input/output device 540. Each of the components 510, 520, 530, and 540 are interconnected using a system bus 540. The processor 510 is capable of processing instructions for execution within the system 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical data for a user interface on the input/output device 540.

The memory 520 stores data within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In one implementation, the input/output device 540 includes a keyboard and/or pointing device. In another implementation, the input/output device 540 includes a display unit for displaying graphical user interfaces.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer system implemented method for predicting a compliance risk of a clinical trial site, the method comprising:
   obtaining, at the computer system, investigation data collected at the clinical trial site;
   training, by one or more processors of the computer system and based on the investigation data collected at the clinical trial site, a set of machine learning models corresponding to the clinical trial site, comprising training a first machine learning model in the set of machine learning models to identify a first set of one or more indicators that indicate the compliance risk; and training a second machine learning model in the set of machine learning models to identify a second set of one or more indicators that indicate the compliance risk;
   determining, by the one or more processors and for the first machine learning model, a first likelihood that the investigation data is associated with the first set of one or more indicators that indicate the compliance risk;
   determining, by the one or more processors and for the second machine learning model, a second likelihood that the investigation data is associated with the second set of one or more indicators that indicate the compliance risk;
   determining that the first likelihood has higher accuracy than the second likelihood;
   based on determining that the first likelihood has higher accuracy than the second likelihood:
      assigning a first weight to the first machine learning model; and
      assigning a second weight to the second machine learning model, wherein the first weight exceeds the second weight; and
   providing, by the one or more processors and for output on a user interface, an indication of the compliance risk of the clinical trial site based on the first and the second weights.

2. The method of claim 1, wherein the compliance risk is associated with a subset of data records identified by the set of machine learning models as representing an adverse event specified by a regulatory agency associated with the investigation data.

3. The method of claim 2, wherein the compliance risk indicates that all of the data records included in the subset of data records have not been reported to the regulatory agency.

4. The method of claim 2, wherein the compliance risk indicates that one or more data records included in the subset of data records have not been reported to the regulatory agency.

5. The method of claim 2, wherein:
   the compliance risk indicates that the subset of data records are likely to be reported to the regulatory agency within a time period that exceeds a threshold time period for reporting the adverse event.

6. The method of claim 5, wherein the threshold time period for reporting the adverse event is defined by (i) a first time point when the adverse event is discovered, and (ii) a second time point during when the adverse event is reported to the regulatory agency.

7. The method of claim 1, further comprising:
combining the first likelihood and the second likelihood to determine the indication of the compliance risk of the clinical trial site.

8. The method of claim 7,
wherein a value of the first weight exceeds a value of the second weight; and
wherein combining the first likelihood and the second likelihood to determine the indication of the compliance risk of the clinical trial site comprises combining the first likelihood and the second likelihood based on the first weight assigned to the first machine learning model and the second weight assigned to the second machine learning model.

9. The method of claim 1, further comprising:
determining that a combined likelihood satisfies a threshold value, wherein the combined likelihood is a likelihood combining the first likelihood and the second likelihood based on the first and the second weights assigned to a respective machine learning model; and
based on determining that the combined likelihood satisfies the threshold value, determining that the clinical trial site is a risk-associated clinical site.

10. The method of claim 1, further comprises:
determining one or more attributes associated with the clinical trial site;
identifying, based on the attributes, one or more machine learning models in the set of machine learning models, wherein each machine learning model in the set of machine learning models is trained to identify, based on historical investigation data collected at the clinical trial site, one or more indicators that indicate the compliance risk of the clinical trial site.

11. A system comprising:
one or more computers and
one or more storage devices storing instructions that are operable, when executed by the one or more computers, to cause the one or more computers to perform operations comprising:
obtaining, at the one or more computers, investigation data collected at the clinical trial site;
training, by the one or more computers and based on the investigation data collected at the clinical trial site, a set of machine learning models corresponding to the clinical trial site,
comprising training a first machine learning model in the set of machine learning models to identify a first set of one or more indicators that indicate the compliance risk; and training a second machine learning model in the set of machine learning models to identify a second set of one or more indicators that indicate the compliance risk;
determining, by the one or more computers and for the first machine learning model, a first likelihood that the investigation data is associated with the first set of one or more indicators that indicate the compliance risk;
determining, by the one or more computers and for the second machine learning model, a second likelihood that the investigation data is associated with the second set of one or more indicators that indicate the compliance risk;
determining that the first likelihood has higher accuracy than the second likelihood;
based on determining that the first likelihood has higher accuracy than the second likelihood:
assigning a first weight to the first machine learning model; and
assigning a second weight to the second machine learning model, wherein the first weight exceeds the second weight; and
providing, by the one or more computers and for output on a user interface, an indication of the compliance risk of the clinical trial site based on the first and the second weights.

12. The system of claim 11, wherein the compliance risk is associated with a subset of data records identified by the set of machine learning models as representing an adverse event specified by a regulatory agency associated with the investigation data.

13. The system of claim 11, wherein the operations further comprise:
combining the first likelihood and the second likelihood to determine the indication of the compliance risk of the clinical trial site.

14. The system of claim 13,
wherein a value of the first weight exceeds a value of the second weight; and
wherein combining the first likelihood and the second likelihood to determine the indication of the compliance risk of the clinical trial site comprises combining the first likelihood and the second likelihood based on the first weight assigned to the first machine learning model and the second weight assigned to the second machine learning model.

15. The system of claim 11, wherein the instructions, when executed, cause the one or more computers to:
determine that a combined likelihood satisfies a threshold value, wherein the combined likelihood is a likelihood combining the first likelihood and the second likelihood based on the first and the second weights assigned to a respective machine learning model; and
based on determining that the combined likelihood satisfies the threshold value, determine that the clinical trial site is a risk-associated clinical site.

16. The system of claim 11, wherein the operations further comprise:
determining one or more attributes associated with the clinical trial site;
identifying, based on the attributes, one or more machine learning models in the set of machine learning models, wherein each machine learning model in the set of machine learning models is trained to identify, based on historical investigation data collected at the clinical trial site, one or more indicators that indicate the compliance risk of the clinical trial site.

17. A non-transitory computer-readable medium storing software comprising instructions executable by one or more computers which, when executed, cause the one or more computers to perform operations comprising:
obtaining, at the one or more computers, investigation data collected at the clinical trial site;
training, by the one or more computers and based on the investigation data collected at the clinical trial site, a set of machine learning models corresponding to the clinical trial site,
comprising training a first machine learning model in the set of machine learning models to identify a first set of one or more indicators that indicate the compliance risk; and training a second machine learning model in the set of machine learning models to identify a second set of one or more indicators that indicate the compliance risk;

determining, by the one or more computers and for the first machine learning model, a first likelihood that the investigation data is associated with the first set of one or more indicators that indicate the compliance risk;

determining, by the one or more computers and for the second machine learning model, a second likelihood that the investigation data is associated with the second set of one or more indicators that indicate the compliance risk;

determining that the first likelihood has higher accuracy than the second likelihood;

based on determining that the first likelihood has higher accuracy than the second likelihood:
    assigning a first weight to the first machine learning model; and
    assigning a second weight to the second machine learning model, wherein the first weight exceeds the second weight; and providing, by the one or more computers and for output on a user interface, an indication of the compliance risk of the clinical trial site based on the first and the second weights.

18. The non-transitory computer-readable medium of claim 17, wherein the compliance risk is associated with a subset of data records identified by the set of machine learning models as representing an adverse event specified by a regulatory agency associated with the investigation data.

19. The non-transitory computer-readable medium of claim 17, wherein the operations further comprise:
    combining the first likelihood and the second likelihood to determine the indication of the compliance risk of the clinical trial site.

20. The non-transitory computer-readable medium of claim 19,
    wherein a value of the first weight exceeds a value of the second weight; and
    wherein combining the first likelihood and the second likelihood to determine the indication of the compliance risk of the clinical trial site comprises combining the first likelihood and the second likelihood based on the first weight assigned to the first machine learning model and the second weight assigned to the second machine learning model.

21. The non-transitory computer-readable medium of claim 17, wherein the instructions, when executed, cause the one or more computers to:
    determine that a combined likelihood satisfies a threshold value, wherein the combined likelihood is a likelihood combining the first likelihood and the second likelihood based on the first and the second weights assigned to a respective machine learning model; and
    based on determining that the combined likelihood satisfies the threshold value, determine that the clinical trial site is a risk-associated clinical site.

22. The non-transitory computer-readable medium of claim 17, wherein the operations further comprise:
    determining one or more attributes associated with the clinical trial site;
    identifying, based on the attributes, one or more machine learning models in the set of machine learning models, wherein each machine learning model in the set of machine learning models is trained to identify, based on historical investigation data collected at the clinical trial site, one or more indicators that indicate the compliance risk of the clinical trial site.

* * * * *